(12) United States Patent
Anderson et al.

(10) Patent No.: US 12,095,940 B2
(45) Date of Patent: Sep. 17, 2024

(54) HEARING DEVICES USING PROXY DEVICES FOR EMERGENCY COMMUNICATION

(71) Applicant: Starkey Laboratories, Inc., Eden Prairie, MN (US)

(72) Inventors: Aaron Anderson, Mayer, MN (US); Alexander Botz, Minnetonka, MN (US); Gregory John Haubrich, Champlin, MN (US); Paul Shriner, Eden Prairie, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 165 days.

(21) Appl. No.: 17/628,439

(22) PCT Filed: Jul. 17, 2020

(86) PCT No.: PCT/US2020/042580
§ 371 (c)(1),
(2) Date: Jan. 19, 2022

(87) PCT Pub. No.: WO2021/016099
PCT Pub. Date: Jan. 28, 2021

(65) Prior Publication Data
US 2022/0286553 A1 Sep. 8, 2022

Related U.S. Application Data

(60) Provisional application No. 62/876,400, filed on Jul. 19, 2019.

(51) Int. Cl.
*H04M 1/72409* (2021.01)
*H04M 1/72418* (2021.01)

(52) U.S. Cl.
CPC . *H04M 1/724094* (2022.02); *H04M 1/72418* (2021.01)

(58) Field of Classification Search
CPC ........ H04M 1/724094; H04M 1/72418; A61B 5/0205; A61B 5/296; A61B 5/297;
(Continued)

(56) References Cited

U.S. PATENT DOCUMENTS

| 5,913,310 A | 6/1999 | Brown |
|---|---|---|
| 6,186,145 B1 | 2/2001 | Brown |

(Continued)

FOREIGN PATENT DOCUMENTS

| EP | 0799597 | 10/1997 |
|---|---|---|
| EP | 1229508 | 8/2002 |

(Continued)

OTHER PUBLICATIONS

"Communication Pursuant to Article 94(3) EPC," for European Patent Application No. 17838110.9 mailed Feb. 1, 2022 (8 pages).

(Continued)

*Primary Examiner* — Angelica Perez
(74) *Attorney, Agent, or Firm* — Pauly, DeVries Smith & Deffner LLC

(57) ABSTRACT

Embodiments herein relate to hearing device systems that can utilize proxy devices to convey emergency communications. In an embodiment, the system operates in a first communication mode and a second communication mode. The first communication mode can include the hearing device being paired to a wireless communication enabled device for conveying data to a non-local network as initiated by the hearing device. The second communication mode can include the hearing device accessory being paired to the wireless communication enabled device for conveying data to the non-local network as initiated by the hearing device.

(Continued)

The system can enter the second communication mode when the hearing device cannot communicate with the wireless communication enabled device. The hearing device accessory uses a hardware address of the hearing device to communicate with the wireless communication enabled device as if it was paired thereto. Other embodiments are also included herein.

20 Claims, 13 Drawing Sheets

(58) Field of Classification Search
CPC ..... A61B 5/6867; A61B 5/742; A61B 5/7455; A61B 2505/07; A61B 2560/029; A61B 2562/0204; A61B 2562/0209; A61B 2562/0219; A61B 2562/0247; A61B 2562/0261; A61B 2562/0271; A61B 2562/08; A61B 5/0022; A61B 5/1117; A61B 5/6815; A61B 5/7405; A61B 5/746; A61B 5/747; H04R 25/554; H04R 2225/55; G08B 21/043; G08B 21/0446; G08B 25/009
See application file for complete search history.

(56) References Cited

U.S. PATENT DOCUMENTS

| | | | |
|---|---|---|---|
| 6,326,918 B1 | 12/2001 | Stewart | |
| 6,475,161 B2 | 11/2002 | Teicher et al. | |
| 6,568,396 B1 | 5/2003 | Anthony | |
| 6,609,523 B1 | 8/2003 | Anthony | |
| 6,647,257 B2 | 11/2003 | Owensby | |
| 6,650,871 B1 | 11/2003 | Cannon et al. | |
| D487,409 S | 3/2004 | Philipson | |
| 6,758,218 B2 | 7/2004 | Anthony | |
| 6,816,878 B1 | 11/2004 | Zimmers et al. | |
| 6,836,667 B1 | 12/2004 | Smith | |
| 7,007,327 B2 | 3/2006 | Ogawa et al. | |
| 7,139,820 B1 | 11/2006 | O'Toole et al. | |
| 7,282,031 B2 | 10/2007 | Hendrich | |
| 7,294,107 B2 | 11/2007 | Simon et al. | |
| 7,411,493 B2 | 8/2008 | Smith | |
| 7,450,954 B2 | 11/2008 | Randall | |
| 7,490,611 B2 | 2/2009 | Bromwich | |
| 7,602,930 B2 | 10/2009 | Kasztelan | |
| 7,612,681 B2 | 11/2009 | Azzaro et al. | |
| 7,682,308 B2 | 3/2010 | Hendrich | |
| 7,742,774 B2 | 6/2010 | Oh et al. | |
| 7,892,180 B2 | 2/2011 | Epley | |
| 7,899,621 B2 | 3/2011 | Breed et al. | |
| 8,092,398 B2 | 1/2012 | Weinberg et al. | |
| 8,150,044 B2 | 4/2012 | Goldstein et al. | |
| 8,162,846 B2 | 4/2012 | Epley | |
| 8,169,938 B2 | 5/2012 | Duchscher et al. | |
| 8,308,665 B2 | 11/2012 | Harry et al. | |
| 8,442,245 B2 | 5/2013 | Wurzbacher et al. | |
| 8,452,273 B1 | 5/2013 | Khomenko et al. | |
| 8,494,507 B1 | 7/2013 | Tedesco et al. | |
| 8,559,914 B2 | 10/2013 | Jones | |
| 8,585,589 B1 | 11/2013 | Cinberg | |
| 8,652,040 B2 | 2/2014 | LeBoeuf et al. | |
| 8,737,951 B2 | 5/2014 | Jones et al. | |
| 9,049,558 B2 | 6/2015 | Jones et al. | |
| 9,149,222 B1 | 10/2015 | Zets et al. | |
| 9,167,356 B2 | 10/2015 | Higgins et al. | |
| 9,179,862 B2 | 11/2015 | Stergiou et al. | |
| 9,216,132 B2 | 12/2015 | Aoki et al. | |
| D747,554 S | 1/2016 | Daniel | |
| 9,226,706 B2 | 1/2016 | Uehara et al. | |
| 9,313,585 B2 | 4/2016 | Lunner | |
| 9,414,784 B1 | 8/2016 | Berme et al. | |
| 9,426,582 B2 | 8/2016 | Pontoppidan | |
| 9,452,101 B2 | 9/2016 | Tomlinson et al. | |
| 9,605,390 B2 | 3/2017 | Penland | |
| 9,607,498 B2 | 3/2017 | Osorio | |
| 9,741,227 B1 | 8/2017 | Kusens | |
| 9,798,860 B1 | 10/2017 | Movva | |
| 9,848,273 B1 | 12/2017 | Helwani et al. | |
| 9,877,668 B1 | 1/2018 | Sarkar et al. | |
| 9,918,663 B2 | 3/2018 | Singhatat | |
| 9,936,916 B2 | 4/2018 | Sahin | |
| 9,992,021 B1 | 6/2018 | Perdomo | |
| 9,999,377 B2 | 6/2018 | Osorio | |
| 10,015,579 B2 | 7/2018 | Boesen | |
| 10,149,798 B2 | 12/2018 | Roth | |
| 10,178,970 B2 | 1/2019 | Oddsson et al. | |
| 10,242,590 B2 | 3/2019 | Yu | |
| 10,258,257 B2 | 4/2019 | Greene | |
| 10,262,517 B2 | 4/2019 | Bobda | |
| 10,271,790 B2 | 4/2019 | Lee | |
| 10,319,209 B2 | 6/2019 | Carlton-Foss | |
| 10,624,559 B2 | 4/2020 | Bhunia et al. | |
| 2002/0188217 A1 | 12/2002 | Farwell | |
| 2004/0234933 A1 | 11/2004 | Dawson et al. | |
| 2005/0046576 A1 | 3/2005 | Julian et al. | |
| 2005/0240378 A1 | 10/2005 | Smith et al. | |
| 2005/0273017 A1 | 12/2005 | Gordon | |
| 2006/0251334 A1 | 11/2006 | Oba et al. | |
| 2006/0282021 A1 | 12/2006 | DeVaul et al. | |
| 2007/0177103 A1 | 8/2007 | Migliaccio et al. | |
| 2007/0197881 A1 | 8/2007 | Wolf et al. | |
| 2007/0200927 A1 | 8/2007 | Krenik | |
| 2008/0009262 A1 | 1/2008 | Rudolf et al. | |
| 2008/0021731 A1 | 1/2008 | Rodgers | |
| 2008/0129518 A1 | 6/2008 | Carlton-Foss | |
| 2008/0146890 A1 | 6/2008 | LeBoeuf et al. | |
| 2008/0186189 A1 | 8/2008 | Azzaro et al. | |
| 2009/0058660 A1 | 3/2009 | Torch | |
| 2009/0240170 A1 | 9/2009 | Rowley et al. | |
| 2009/0240172 A1 | 9/2009 | Fernandez et al. | |
| 2009/0299622 A1 | 12/2009 | Denaro | |
| 2009/0322513 A1 | 12/2009 | Hwang et al. | |
| 2010/0010832 A1 | 1/2010 | Boute et al. | |
| 2010/0063889 A1* | 3/2010 | Proctor, Jr. ............. H04L 63/20 |
| | | | 705/26.1 |
| 2010/0075806 A1 | 3/2010 | Montgomery | |
| 2010/0141439 A1 | 6/2010 | Lunner | |
| 2010/0179389 A1 | 7/2010 | Moroney et al. | |
| 2012/0092156 A1 | 4/2012 | Tran | |
| 2012/0101411 A1 | 4/2012 | Hausdorff et al. | |
| 2012/0119904 A1 | 5/2012 | Boone et al. | |
| 2012/0219180 A1 | 8/2012 | Mehra | |
| 2013/0065569 A1 | 3/2013 | Leipzig et al. | |
| 2013/0091016 A1 | 4/2013 | Shutter | |
| 2013/0135097 A1 | 5/2013 | Doezema | |
| 2013/0278707 A1* | 10/2013 | Yang ...................... H04W 4/80 |
| | | | 348/14.02 |
| 2013/0343584 A1 | 12/2013 | Bennett et al. | |
| 2013/0343585 A1 | 12/2013 | Bennett et al. | |
| 2014/0002586 A1 | 1/2014 | Nourbakhsh | |
| 2014/0023216 A1 | 1/2014 | Solum et al. | |
| 2014/0024972 A1 | 1/2014 | Greene | |
| 2014/0064528 A1 | 3/2014 | Flood et al. | |
| 2014/0074180 A1 | 3/2014 | Heldman et al. | |
| 2014/0148733 A1 | 5/2014 | Stone et al. | |
| 2014/0266988 A1 | 9/2014 | Fisher et al. | |
| 2014/0276238 A1 | 9/2014 | Osorio | |
| 2015/0018724 A1 | 1/2015 | Hsu et al. | |
| 2015/0040685 A1 | 2/2015 | Nicholson et al. | |
| 2015/0112162 A1 | 4/2015 | Wilmink | |
| 2015/0164383 A1 | 6/2015 | Varsavsky et al. | |
| 2015/0196231 A1 | 7/2015 | Ziaie et al. | |
| 2015/0209212 A1 | 7/2015 | Duguid | |
| 2015/0257662 A1 | 9/2015 | Lee et al. | |
| 2015/0319546 A1 | 11/2015 | Sprague | |
| 2015/0351690 A1 | 12/2015 | Toth et al. | |
| 2016/0029938 A1 | 2/2016 | Shudo | |
| 2016/0033280 A1 | 2/2016 | Moore et al. | |
| 2016/0070122 A1 | 3/2016 | Sales et al. | |
| 2016/0100776 A1 | 4/2016 | Najafi et al. | |
| 2016/0155312 A1 | 6/2016 | Osorio | |
| 2016/0262608 A1 | 9/2016 | Krueger | |

(56) References Cited

U.S. PATENT DOCUMENTS

| | | | |
|---|---|---|---|
| 2016/0263437 A1 | 9/2016 | Kow et al. | |
| 2016/0275805 A1 | 9/2016 | Reichow | |
| 2016/0295978 A1 | 10/2016 | Hyde et al. | |
| 2017/0000387 A1 | 1/2017 | Forth et al. | |
| 2017/0006931 A1 | 1/2017 | Guez et al. | |
| 2017/0007147 A1 | 1/2017 | Hasegawa | |
| 2017/0071532 A1 | 3/2017 | Greco | |
| 2017/0112671 A1 | 4/2017 | Goldstein | |
| 2017/0116846 A1 | 4/2017 | Wengrovitz et al. | |
| 2017/0127196 A1 | 5/2017 | Blum et al. | |
| 2017/0134102 A1 | 5/2017 | Okumura et al. | |
| 2017/0140637 A1 | 5/2017 | Thurlow et al. | |
| 2017/0156965 A1 | 6/2017 | Geisinger et al. | |
| 2017/0169716 A1 | 6/2017 | Super et al. | |
| 2017/0172465 A1 | 6/2017 | Osorio | |
| 2017/0188895 A1 | 7/2017 | Nathan | |
| 2017/0197115 A1 | 7/2017 | Cook et al. | |
| 2017/0229041 A1 | 8/2017 | Reichow et al. | |
| 2017/0238103 A1* | 8/2017 | Gehring | H04W 4/80 381/23.1 |
| 2017/0273616 A1 | 9/2017 | Yang et al. | |
| 2017/0274219 A1 | 9/2017 | Ernst et al. | |
| 2017/0291065 A1 | 10/2017 | Klopman | |
| 2017/0352240 A1 | 12/2017 | Carlton-Foss | |
| 2017/0358195 A1 | 12/2017 | Bobda | |
| 2017/0358241 A1 | 12/2017 | Wexler et al. | |
| 2017/0360364 A1 | 12/2017 | Heasman et al. | |
| 2018/0000385 A1 | 1/2018 | Heaton et al. | |
| 2018/0092572 A1 | 4/2018 | Sanchez et al. | |
| 2018/0093121 A1 | 4/2018 | Matsuura et al. | |
| 2018/0132757 A1 | 5/2018 | Kong et al. | |
| 2018/0177436 A1 | 6/2018 | Chang et al. | |
| 2018/0184907 A1 | 7/2018 | Tran | |
| 2018/0220353 A1* | 8/2018 | Mendiola | H04W 24/02 |
| 2018/0220974 A1 | 8/2018 | Schuman et al. | |
| 2018/0228404 A1 | 8/2018 | Bhunia et al. | |
| 2018/0228405 A1 | 8/2018 | Burwinkel et al. | |
| 2018/0233018 A1 | 8/2018 | Burwinkel et al. | |
| 2018/0233028 A1 | 8/2018 | Rhoads et al. | |
| 2018/0234781 A1 | 8/2018 | Stewart et al. | |
| 2018/0242859 A1 | 8/2018 | LeBoeuf et al. | |
| 2018/0250494 A1 | 9/2018 | Hanbury | |
| 2018/0279915 A1 | 10/2018 | Huang et al. | |
| 2018/0279919 A1 | 10/2018 | Bansbach et al. | |
| 2018/0289287 A1 | 10/2018 | Sio et al. | |
| 2018/0317837 A1 | 11/2018 | Burwinkel et al. | |
| 2018/0341582 A1 | 11/2018 | Moon et al. | |
| 2018/0343527 A1 | 11/2018 | Edwards | |
| 2019/0090812 A1* | 3/2019 | Martin | G06F 1/3231 |
| 2019/0117121 A1 | 4/2019 | Kutina et al. | |
| 2019/0246890 A1 | 8/2019 | Kerasidis et al. | |
| 2020/0138364 A1 | 5/2020 | Fabry et al. | |
| 2020/0143703 A1 | 5/2020 | Fabry et al. | |
| 2020/0205746 A1 | 7/2020 | Burwinkel et al. | |
| 2020/0219373 A1 | 7/2020 | Stut et al. | |
| 2020/0236479 A1 | 7/2020 | Burwinkel et al. | |

FOREIGN PATENT DOCUMENTS

| | | |
|---|---|---|
| EP | 1628504 | 2/2006 |
| EP | 2104366 | 9/2009 |
| EP | 2700907 | 2/2014 |
| EP | 2725818 | 4/2014 |
| EP | 2983379 | 2/2016 |
| EP | 3075306 | 10/2016 |
| EP | 3131027 | 2/2017 |
| EP | 1983896 | 6/2017 |
| EP | 3246888 | 11/2017 |
| EP | 3328277 | 6/2018 |
| EP | 3346402 | 7/2018 |
| EP | 3402218 | 11/2018 |
| EP | 3591990 | 1/2020 |
| EP | 3669765 | 6/2020 |
| WO | 2008143908 | 11/2008 |
| WO | 2009053184 | 4/2009 |
| WO | 2010046504 | 4/2010 |
| WO | 2010049543 | 5/2010 |
| WO | WO 2010108287 | * 9/2010 |
| WO | 2012083102 | 6/2012 |
| WO | 2014184395 | 11/2014 |
| WO | 2015164456 | 10/2015 |
| WO | 2016088027 | 6/2016 |
| WO | 2016097746 | 6/2016 |
| WO | 2016110804 | 7/2016 |
| WO | 2016123129 | 8/2016 |
| WO | 2017023864 | 2/2017 |
| WO | 2018127851 | 7/2018 |
| WO | 2018147942 | 8/2018 |
| WO | 2018147943 | 8/2018 |
| WO | 2018148713 | 8/2018 |
| WO | 2018223505 | 12/2018 |
| WO | 2019073473 | 4/2019 |
| WO | 2019086997 | 5/2019 |
| WO | 2020097353 | 5/2020 |
| WO | 2020097355 | 5/2020 |
| WO | 2020124022 | 6/2020 |
| WO | 2020139850 | 7/2020 |
| WO | 2020206155 | 10/2020 |
| WO | 2021016099 | 1/2021 |

OTHER PUBLICATIONS

"European Search Report," for European Patent Application No. 19212657.1 mailed Feb. 14, 2020 (10 pages).

"Final Office Action," for U.S. Appl. No. 15/858,630 mailed Mar. 21, 2019 (15 pages).

"Final Office Action," for U.S. Appl. No. 15/858,680 mailed May 10, 2021 (23 pages).

"Final Office Action," for U.S. Appl. No. 15/858,680 mailed May 21, 2020 (11 pages).

"Final Office Action," for U.S. Appl. No. 15/895,311 mailed Apr. 13, 2021 (9 pages).

"Final Office Action," for U.S. Appl. No. 15/895,311 mailed Jul. 17, 2020 (18 pages).

"International Preliminary Report on Patentability," for PCT Application No. PCT/US2017/069026 mailed Aug. 22, 2019 (9 pages).

"International Preliminary Report on Patentability," for PCT Application No. PCT/US2017/0690365 mailed Aug. 22, 2019 (9 pages).

"International Preliminary Report on Patentability," for PCT Application No. PCT/US2018/017944 mailed Aug. 22, 2019 (7 pages).

"International Preliminary Report on Patentability," for PCT Application No. PCT/US2019/066358 mailed Jun. 24, 2021 (12 pages).

"International Preliminary Report on Patentability," for PCT Application No. PCT/US2019/068397 mailed Jul. 8, 2021 (9 pages).

"International Preliminary Report on Patentability," for PCT Application No. PCT/US2020/026435 mailed Oct. 14, 2021 (8 pages).

"International Preliminary Report on Patentability," for PCT Application No. PCT/US2020/042580 mailed Feb. 3, 2022 (15 pages).

"International Search Report and Written Opinion," for PCT Application No. PCT/US2017/069026 mailed Apr. 3, 2018 (16 pages).

"International Search Report and Written Opinion," for PCT Application No. PCT/US2017/069035 mailed Apr. 3, 2018 (16 pages).

"International Search Report and Written Opinion," for PCT Application No. PCT/US2018/017944 mailed Apr. 26, 2018 (12 pages).

"International Search Report and Written Opinion," for PCT Application No. PCT/US2019/060296 mailed Apr. 14, 2020 (14 pages).

"International Search Report and Written Opinion," for PCT Application No. PCT/US2019/060298 mailed Apr. 28, 2020 (20 pages).

"International Search Report and Written Opinion," for PCT Application No. PCT/US2019/066358 mailed Jun. 23, 2020 (18 pages).

"International Search Report and Written Opinion," for PCT Application No. PCT/US2019/068397 mailed Apr. 14, 2020 (14 pages).

"International Search Report and Written Opinion," for PCT Application No. PCT/US2020/026435 mailed Jul. 9, 2020 (12 pages).

"International Search Report and Written Opinion," for PCT Application No. PCT/US2020/042580 mailed Oct. 23, 2020 (20 pages).

"Invitation to Pay Additional Fees and, Where Applicable, Protest Fee," for PCT Application No. PCT/US2019/066358 mailed Mar. 5, 2020 (12 pages).

(56) References Cited

OTHER PUBLICATIONS

"Non Final Office Action," for U.S. Appl. No. 15/589,298 mailed Jan. 2, 2019 (8 pages).
"Non Final Office Action," for U.S. Appl. No. 15/858,630 mailed Sep. 4, 2018 (13 pages).
"Non-Final Office Action," for U.S. Appl. No. 15/589,298 mailed Jul. 11, 2019 (13 pages).
"Non-Final Office Action," for U.S. Appl. No. 15/589,298 mailed May 19, 2020 (15 pages).
"Non-Final Office Action," for U.S. Appl. No. 15/858,680 mailed Dec. 22, 2020 (22 pages).
"Non-Final Office Action," for U.S. Appl. No. 15/858,680 mailed Jan. 16, 2020 (25 pages).
"Non-Final Office Action," for U.S. Appl. No. 15/895,311 mailed Feb. 9, 2022 (17 pages).
"Non-Final Office Action," for U.S. Appl. No. 15/895,311 mailed Feb. 23, 2021 (12 pages).
"Non-Final Office Action," for U.S. Appl. No. 15/895,311 mailed Mar. 17, 2020 (26 pages).
"Non-Final Office Action," for U.S. Appl. No. 16/714,339 mailed May 17, 2021 (34 pages).
"Non-Final Office Action," for U.S. Appl. No. 16/725,766 mailed Oct. 8, 2021 (30 pages).
"Notice of Allowance," for U.S. Appl. No. 15/589,298 mailed Jan. 22, 2020 (12 pages).
"Notice of Allowance," for U.S. Appl. No. 15/858,630 mailed Jul. 22, 2019 (10 pages).
"Notice of Allowance," for U.S. Appl. No. 15/858,630 mailed Nov. 1, 2019 (10 pages).
"Notice of Allowance," for U.S. Appl. No. 16/714,339 mailed Nov. 2, 2021 (13 pages).
"Response to Final Office Action," for U.S. Appl. No. 15/858,630 filed with the USPTO Jun. 20, 2019 (11 pages).
"Response to Final Office Action," for U.S. Appl. No. 15/858,680, filed Oct. 8, 2021 (9 pages).
"Response to Final Office Action," for U.S. Appl. No. 15/858,680, filed Oct. 21, 2020 (11 pages).
"Response to Final Office Action," for U.S. Appl. No. 15/895,311, filed Oct. 19, 2020 (13 pages).
"Response to Final Office Action," for U.S. Appl. No. 15/895,311, filed Sep. 13, 2021 (7 pages).
"Response to Non Final Office Action," for U.S. Appl. No. 15/589,298 filed with the USPTO Apr. 1, 2019 (8 pages).
"Response to Non-Final Office Action," for U.S. Appl. No. 15/589,298, filed Aug. 19, 2020 (14 pages).
"Response to Non-Final Office Action," for U.S. Appl. No. 15/589,298 filed with the USPTO Oct. 3, 2019 (12 pages).
"Response to Non-Final Office Action," for U.S. Appl. No. 15/858,680, filed Apr. 16, 2020 (8 pages).
"Response to Non-Final Office Action," for U.S. Appl. No. 15/858,680, filed Mar. 22, 2021 (15 pages).
"Response to Non-Final Office Action," for U.S. Appl. No. 15/895,311, filed Jun. 12, 2020 (10 pages).
"Response to Non-Final Office Action," for U.S. Appl. No. 15/895,311, filed Mar. 17, 2021 (7 pages).
"Response to Non-Final Office Action," for U.S. Appl. No. 16/714,339, filed Sep. 15, 2021 (6 pages).
"Response to Non-Final Office Action," for U.S. Appl. No. 15/858,630 filed with the USPTO Dec. 3, 2018 (11 pages).
EP Search Report dated Oct. 8, 2018 from EP App. No. 18171323.1, 10 pages.
PathVU Mobile App, Pathway Accessibility Solutions, Inc., Pittsburgh, Pennsylvania [retrieved on Jun. 19, 2018. Retrieved from the Internet:<URL: http://www.pathvu.com/>; 6 pgs.
Leake, Jason Llewellyn "Fall Detectors for People with Dementia," University of Bath Student Thesis, Jun. 2016 (364 pages).

Zheng, et al. "Effect of postural changes on lower limb blood volume, detected with non-invasive photoplethysmography," Journal of Medical Engineering & Technology, vol. 32, No. 5, Sep./Oct. 2008, pp. 358-364 (7 pages).
"Sonos Boost Wireless Extender," Sonos Product available at least as early as 2014 URL<https://www.sonos.com/en-us/shop/boost>, retrieved Feb. 22, 2022 (4 pages).
Barber & Stockwell "Manual of Electronystagmography," Jan. 1980, C.V. Mosby Company, St. Louis, Missouri, Cover page, copyright page, and table of contents; total of 3 pages.
Buatois, et al. "Posturography and Risk of Recurrent Falls in Healthy Non-Institutionalized Persons Aged Over 65," Gerontology, Aug. 2006; 52(6):345-352 (8 pages).
Choi, W. J., et al. "Effect of Neck Flexor Muscle Activation on Impact Velocity of the Head During Backward Falls in Young Adults," Clinical Biomechanics 49, Nov. 2017, pp. 28-33.
Coburn, Courtney, et al. "The Comfort Bud: Designed with Patients in Mind," Starkey Hearing Technologies Product Sheet, May 2017 (2 pages).
Da Costa, et al. "Can Falls Risk Prediction Tools Correctly Identify Fall-Prone Elderly Rehabilitation Inpatients? A Systematic Review and Meta-Analysis," PLoS One, Jul. 2012; 7(7):e41061 (8 pages).
El Miedany, et al. "Falls Risk Assessment Score (FRAS): Time to Rethink," Journal of Clinical Gerontology & Geriatrics, Mar. 2011; 2(1):21-26 (6 pages).
Farrell, Lisa, et al. "Vestibular Rehabilitation: An Effective, Evidence-Based Treatment," Vestibular Disorders Association, available as early as Mar. 27, 2016 (11 pages).
Hendrich, Ann L., et al. "Validation of the Hendrich II Fall Risk Model: A Large Concurrent Case/Control Study of Hospitalized Patients," Applied Nursing Research, vol. 16, No. 1 Feb. 2003: pp. 9-21 (13 pages).
Hendrich, Ann, et al. "Hospital Falls: Development of a Predictive Model for Clinical Practice," Applied Nursing Research, vol. 8, No. 3 Aug. 1995: pp. 129-139 (11 pages).
Horak "Postural Orientation and Equilibrium: What do we Need to Know About Neural Control of Balance to Prevent Falls?," Age and Ageing, Sep. 2006; 35-S2:ii7-ii11 (5 pages).
Howcroft, et al. "Review of Fall Risk Assessment in Geriatric Populations using Inertial Sensors," J Neuroeng Rehab, Aug. 2013; 10:91 (12 pages).
Howcroft, et al. "Understanding Dynamic Stability From Pelvis Accelerometer Data and the Relationship to Balance and Mobility in Transtibial Amputees," Gait Posture, Mar. 2015; 41(3): 808-812 (5 pages).
Klenk, et al. "Conceptualizing a Dynamic Fall Risk Model Including Intrinsic Risks and Exposures," JAMDA, Nov. 1, 2017; 18:921-927 (7 pages).
Marschollek, et al. "Predicting In-Patient Falls in a Geriatric Clinic: a Clinical Study Combining Assessment Data and Simple Sensory Gait Measurements," Z Gerontol Geriatr, Jun. 2009; 42(4):317-321 (6 pages).
Oliver "Falls Risk-Prediction Tools for Hospital Inpatients. Time to Put Them to Bed?," Age and Ageing, May 2008; 37:248-250 (3 pages).
Rumalla, et al. "The Effect of Hearing Aids on Postural Stability," Laryngoscope, Mar. 2015; 125(3):720-723 (4 pages).
Salisbury, Joseph P., et al. "Patient Engagement Platform for Remote Monitoring of Vestibular Rehabilitation with Applications in Concussion Management and Elderly Fall Prevention," 2018 IEEE International Conference on Healthcare Informatics, Jun. 2018, pp. 422-423.
Viikki "Machine Learning on Otoneurological Data: Decision Trees for Vertigo Diseases," Academic Dissertation, University of Tampere, Finland, Jun. 2002; 84 pages.
Yang, et al. "Fall Risk Assessment and Early-Warning for Toddler Behaviors at Home," Sensors, Dec. 2013; 13:16985-17005 (21 pages).

\* cited by examiner

HEARING DEVICES USING PROXY DEVICES FOR EMERGENCY COMMUNICATION

This application is being filed as a PCT International Patent application on Jul. 17, 2020, in the name of Starkey Laboratories, Inc., a U.S. national corporation, applicant for the designation of all countries, and Aaron Anderson, a U.S. Citizen, and Alexander Botz, a U.S. Citizen, and Gregory John Haubrich, a U.S. Citizen, and Paul Shriner, a U.S. Citizen, inventors for the designation of all countries, and claims priority to U.S. Provisional Patent Application No. 62/876,400 filed Jul. 19, 2019, the contents of which are herein incorporated by reference in its entirety.

FIELD

Embodiments herein relate to hearing device systems with capabilities for emergency communication. In particular, embodiments herein relate to hearing device systems that can utilize proxy devices to convey emergency communications.

BACKGROUND

Falls are the second leading cause of accidental or unintentional injury deaths worldwide. Falls happen to people of all ages but are especially prevalent in the elderly. Falls may result from vestibular system disorders, balance disorders, adverse reactions to medications, syncope, cardiac events, and various incapacitating conditions. Beyond falls, there are also many other conditions may lead to an acute emergency or need for urgent help.

In many cases, recovery from a fall and/or an acute emergency condition may require the assistance of a third party. As such, there may be a need to provide a request for assistance or other similar signal to a third party. However, the individual who falls or suffers a rapid onset condition may not be in condition to request assistance. In some cases, devices have been used to summon assistance.

SUMMARY

Embodiments herein relate to hearing device systems that can utilize proxy devices to convey emergency communication. In a first aspect, a hearing device system is included having a hearing device can include a control circuit, a motion sensor in electrical communication with the control circuit, a microphone in electrical communication with the control circuit, an electroacoustic transducer for generating sound in electrical communication with the control circuit, a transceiver in electrical communication with the control circuit, a power supply circuit in electrical communication with the control circuit, and a hearing device accessory. The system can operate in a first communication mode and a second communication mode. The first communication mode can include the hearing device being paired to a wireless communication enabled device for conveying data to a non-local network as initiated by the hearing device. The system can enter the first communication mode when the hearing device can communicate with the wireless communication enabled device. The second communication mode can include the hearing device accessory being paired to the wireless communication enabled device for conveying data to the non-local network as initiated by the hearing device. The system can enter the second communication mode when the hearing device cannot communicate with the wireless communication enabled device. The hearing device accessory can use a hardware address of the hearing device to communicate with the wireless communication enabled device as if it was paired thereto.

In a second aspect, in addition to one or more of the preceding or following aspects, or in the alternative to some aspects, the hearing device accessory can include at least one of a charger, a cell phone transmitter, a media streamer, a hearing aid remote, a USB dongle device, and a remote microphone.

In a third aspect, in addition to one or more of the preceding or following aspects, or in the alternative to some aspects, the wireless communication enabled device can include a smart phone.

In a fourth aspect, in addition to one or more of the preceding or following aspects, or in the alternative to some aspects, the system can further include a second hearing device.

In a fifth aspect, in addition to one or more of the preceding or following aspects, or in the alternative to some aspects, the system can operate in the second communication mode when the hearing device and the second hearing device cannot communicate with the wireless communication enabled device.

In a sixth aspect, in addition to one or more of the preceding or following aspects, or in the alternative to some aspects, the conveyed data can relate to a notification of a possible emergency event.

In a seventh aspect, in addition to one or more of the preceding or following aspects, or in the alternative to some aspects, the conveyed data can relate to a notification of a possible fall event.

In an eighth aspect, in addition to one or more of the preceding or following aspects, or in the alternative to some aspects, the possible fall event can be identified based on data from the motion sensor.

In a ninth aspect, in addition to one or more of the preceding or following aspects, or in the alternative to some aspects, the conveyed data can include a command sent using GATT.

In a tenth aspect, in addition to one or more of the preceding or following aspects, or in the alternative to some aspects, the communication between the hearing device and the wireless communication enabled device or communication between the hearing device accessory and the wireless communication enabled device can be conducted with a low energy wireless protocol.

In an eleventh aspect, in addition to one or more of the preceding or following aspects, or in the alternative to some aspects, the non-local network can include a packet-switched data network.

In a twelfth aspect, in addition to one or more of the preceding or following aspects, or in the alternative to some aspects, the wireless communication enabled device can attempt to provide a confirmation back to the hearing device wearer that it has conveyed data to the non-local network.

In a thirteenth aspect, in addition to one or more of the preceding or following aspects, or in the alternative to some aspects, the system can operate in the second communication mode when the hearing device is unable to establish a link to the wireless communication enabled device.

In a fourteenth aspect, in addition to one or more of the preceding or following aspects, or in the alternative to some aspects, the system can operate in the second communication mode when the hearing device is unable to establish a link to the wireless communication enabled device due to at least one of: the hearing device is disposed at a distance from the wireless communication enabled device that exceeds a maximum communication distance between the hearing device and the wireless communication enabled device, shadowing, interference, and multipath fading.

In a fifteenth aspect, in addition to one or more of the preceding or following aspects, or in the alternative to some aspects, the hearing device can periodically send advertising data packets to test communication between the hearing device and the wireless communication enabled device.

In a sixteenth aspect, in addition to one or more of the preceding or following aspects, or in the alternative to some aspects, the hearing device accessory can periodically scan for advertising data packets sent from the hearing device.

In a seventeenth aspect, in addition to one or more of the preceding or following aspects, or in the alternative to some aspects, the hearing device accessory can use an encryption key of the hearing device in order to pair with the wireless communication enabled device.

In an eighteenth aspect, in addition to one or more of the preceding or following aspects, or in the alternative to some aspects, the hardware address of the hearing device and the encryption key of the hearing device can be stored in non-volatile memory of the hearing device accessory.

In a nineteenth aspect, in addition to one or more of the preceding or following aspects, or in the alternative to some aspects, the system can operate in the second communication mode by including a fall event flag with advertising data sent by the hearing device.

In a twentieth aspect, in addition to one or more of the preceding or following aspects, or in the alternative to some aspects, the system can operate in the second communication mode by including a fall event flag with a non-advertising communication sent by the hearing device.

In a twenty-first aspect, in addition to one or more of the preceding or following aspects, or in the alternative to some aspects, the system can disconnect from all non-essential devices upon entering the second communication mode.

In a twenty-second aspect, in addition to one or more of the preceding or following aspects, or in the alternative to some aspects, all non-essential advertising data from the hearing device can be removed upon entering the second communication mode.

In a twenty-third aspect, in addition to one or more of the preceding or following aspects, or in the alternative to some aspects, a radio transmitter power of the hearing device and the hearing device accessory can be increased to a maximum supported level after a possible fall event is detected by the system.

In a twenty-fourth aspect, in addition to one or more of the preceding or following aspects, or in the alternative to some aspects, intervals between advertising packet transmissions can be reduced after a possible fall event is detected by the system.

In a twenty-fifth aspect, in addition to one or more of the preceding or following aspects, or in the alternative to some aspects, the hearing device can send advertising packets encoded with forward error correction after a possible fall event is detected by the system.

In a twenty-sixth aspect, in addition to one or more of the preceding or following aspects, or in the alternative to some aspects, the hardware address of the hearing device includes a hardware address uniquely assigned to the hearing device at the time of manufacture.

In a twenty-seventh aspect, a method of conveying emergency notifications from a hearing device is included. The method can include detecting a possible fall or other emergency event with the hearing device, sending advertising packets or other communications from the hearing device including an emergency flag if a possible fall or other emergency event when an emergency event is detected, detecting whether communication exists between the hearing device and a wireless communication enabled device, sending an emergency data transmission from the hearing device to the wireless communication enabled device and onto a non-local data communication network when communication exists between the hearing device and the wireless communication enabled device, detecting whether communication exists between the hearing device and a hearing device accessory, and sending an emergency data transmission from the hearing device to the hearing device accessory and onto the wireless communication enabled device and a non-local data communication network when communication exists between the hearing device and the hearing device accessory.

In a twenty-eighth aspect, a method of conveying emergency notifications from a hearing device is included. The method can include detecting a possible fall or other emergency event with the hearing device, sending advertising packets or other communications from the hearing device including an emergency flag if a possible fall or other emergency event when an emergency event is detected, detecting whether communication exists between the hearing device and a wireless communication enabled device, sending an emergency data transmission from the hearing device to the wireless communication enabled device and onto a non-local data communication network when communication exists between the hearing device and the wireless communication enabled device, detecting whether communication exists between the hearing device and a first hearing device accessory, and sending an emergency data transmission from the hearing device to the first hearing device accessory, from the first hearing device accessory to a second hearing device accessory and onto the wireless communication enabled device and a non-local data communication network when communication exists between the hearing device and the first hearing device accessory.

In a twenty-ninth aspect, a hearing device system is included. The system can include a hearing device accessory. The system can operate in a first communication mode and a second communication mode. The first communication mode can include a hearing device being paired to a wireless communication enabled device for conveying data to a non-local network as initiated by the hearing device. The system can operate in the first communication mode when the hearing device can communicate with the wireless communication enabled device. The second communication mode can include the hearing device accessory being paired to the wireless communication enabled device for conveying data to the non-local network as initiated by the hearing device. The system can operate in the second communication mode when the hearing device cannot communicate with the wireless communication enabled device. The hearing device accessory can use a hardware address of the hearing device to communicate with the wireless communication enabled device as if it was paired thereto.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
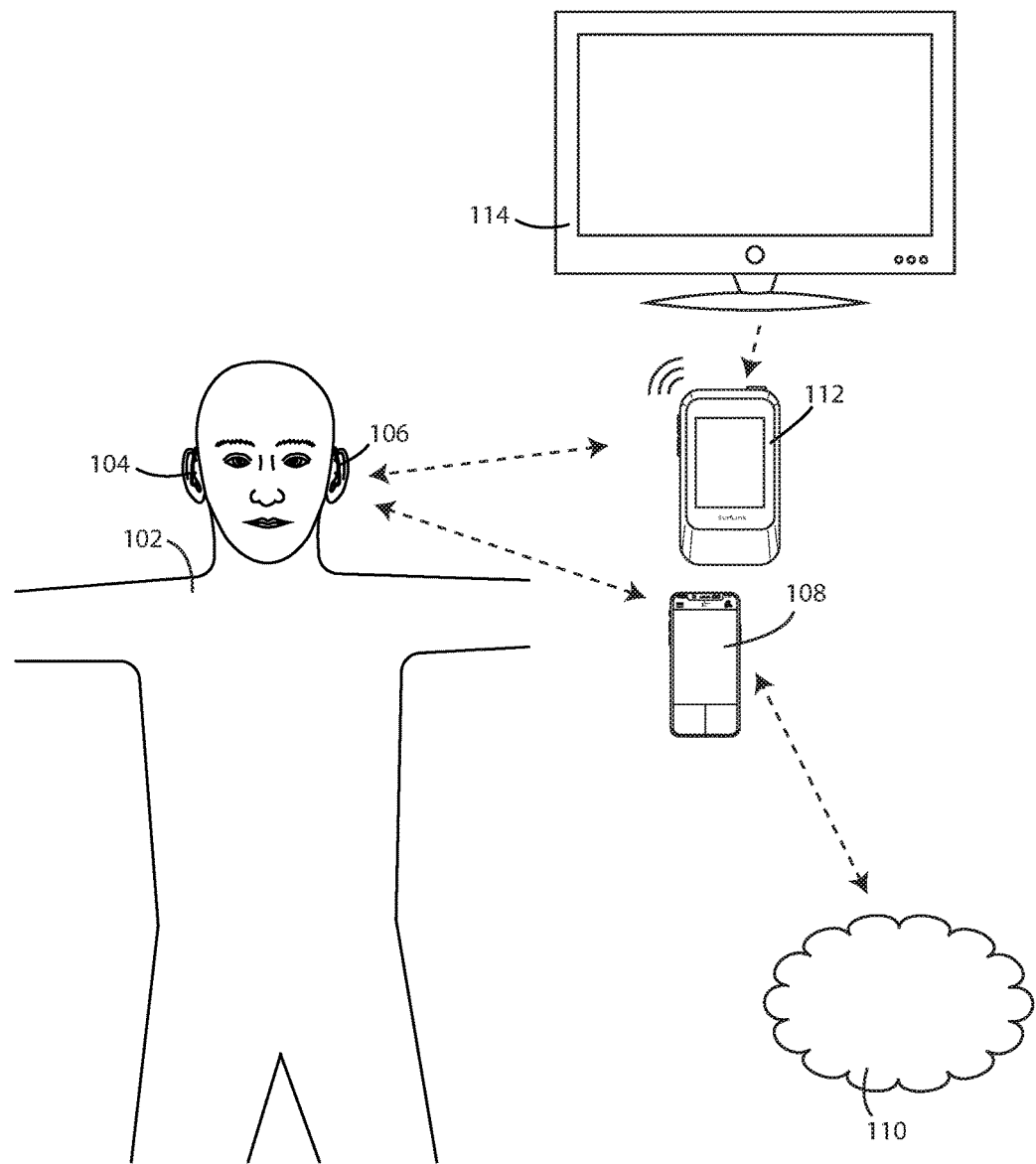
FIG. 1 is a schematic view of components of a hearing device system in accordance with embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As referenced above, there may be a need to provide a request for assistance or other similar signal to a third party. However, the individual who falls or suffers a rapid onset condition may not be in condition to request assistance.

In some cases, devices may be used to summon assistance. However, this places a great degree of importance on the robustness of the communication system used by the device. Unfortunately, communication with wireless signals suffers from various limitations including distance, shadowing, multipath fading and the like.

Hearing devices can be uniquely suitable for identifying a condition (a fall, an acute emergency condition, etc.) that may require the assistance of a third party. However, hearing devices are frequently designed with compact form factors, so power and antenna size may be limited, which may not result in desired wireless communication capability for emergency scenarios.

In accordance with various embodiments herein, a hearing device system is included that can provide robust wireless communication capabilities for emergency scenarios. By way of example, the system can operate in a first communication mode and a second communication mode. The first communication mode can include a hearing device being paired to a wireless communication enabled device (such as a smart phone) for conveying data to a non-local network as initiated by the hearing device. The system can operate in the first communication mode when the hearing device can communicate with the wireless communication enabled device. In some cases, the first communication mode can be the default communication mode.

The second communication mode can include a hearing device accessory acting as if paired to the wireless communication enabled device for conveying data to the non-local network as initiated by the hearing device. For example, the hearing device can send communications to the hearing device accessory, which can then send communications on to the wireless communication enabled device (directly or indirectly) and out to a non-local network.

The system can enter the second communication mode when the hearing device cannot communicate with the wireless communication enabled device or when communication between the hearing device and the wireless communication enabled device is limited. In some embodiments, the hearing device accessory can use a hardware address of the hearing device to act as if it was paired to the wireless communication enabled device and, therefore, allow direct communication between the hearing device and the wireless communication enabled device. As such, the hearing device accessory can serve as a proxy for hearing device within the communication network, effectively introducing more nodes into the network allowing for more robust emergency communication.

The term "hearing device" as used herein shall refer to devices that can aid a person with impaired hearing. The term "hearing device" shall also refer to devices that can produce optimized or processed sound for persons with normal hearing. Hearing devices herein can include hearing assistance devices. Hearing devices herein can include, but are not limited to, behind-the-ear (BTE), in-the ear (ITE), in-the-canal (ITC), invisible-in-canal (IIC), receiver-in-canal (RIC), receiver in-the-ear (RITE) and completely-in-the-canal (CIC) type hearing assistance devices. In some embodiments, the hearing device can be a hearing aid falling under 21 C.F.R. § 801.420. In another example, the hearing device can include one or more Personal Sound Amplification Products (PSAPs). In another example, the hearing device can include one or more cochlear implants, cochlear implant magnets, cochlear implant transducers, and cochlear implant processors. In another example, the hearing device can include one or more "hearable" devices that provide various types of functionality. In other examples, hearing devices can include other types of devices that are wearable in, on, or in the vicinity of the user's ears. In various embodiments, the hearing device can include an ear-worn device. In other examples, hearing devices can include other types of devices that are implanted or otherwise osseointegrated with the user's skull; wherein the device is able to facilitate stimulation of the wearer's ears via the bone conduction pathway.

Referring now to FIG. 1, a schematic view is shown of components of a hearing device system in accordance with embodiments herein. The hearing device system can include a first hearing device 104 and a second hearing device 106 worn by a device wearer 102. While two hearing devices are shown in FIG. 1, it will be appreciated that various hearing device systems herein may only include a single hearing device.

The hearing device system can also include a wireless communication enabled device 108. In some embodiments, the wireless communication enabled device 108 can be a telephony device, such as a smart phone. In some embodiments, the wireless communication enabled device 108 can be can serve as a gateway to a non-local network (such as a non-local packet switched network) including, but not limited to, the internet which can provide communication with sites and/or remote computing resources sometimes referred to as the cloud 110.

The hearing device system can also include a hearing device accessory 112 or a plurality of accessory devices. In some cases, the hearing device accessory 112 can be a TV streamer that facilitates providing audio from a device such as a TV 114 including an audio output on to a device wearer 102 via the hearing devices 104, 106.

In various embodiments, one or both of the hearing devices 104, 106 can be "paired" to the wireless communication enabled device 108. In various embodiments, the term "pairing" can be used to describe the establishment of a trusted relationship between two devices for the purposes of exchanging communications. In some scenarios, "pairing" between two devices may require entering a special operational mode known as a pairing mode wherein one or both devices search for other devices within wireless communication proximity with which to pair. In many cases, authentication may take place by requiring a user to physically enter a code on one device that is generated by or otherwise displayed on the other device. The pairing procedure can then include the exchange of data including, for example, unique ID(s) such as a uniquely assigned hardware address (such as a MAC address, burned-in address, ethernet hardware address, hardware address, physical address, etc.), custom ID(s), and the like.

In some scenarios, the pairing process can progress through phases. For example, in a first phase the devices may read Attribution Protocol (ATT) values to determine which pairing method can be used based on the capabilities of the devices. In a second phase, a Short Term Key (STK) or a Long Term Key (LTK) can be generated based on a Temporary Key (TK) and random numbers. In a third phase, the STK can be used to securely distribute other keys needed for communication such as a Connection Signature Resolving Key (CSRK) for data signing and an Identity Resolving Key (IRK) for private MAC address generation and lookup. Pairing methods can include numeric comparison, just works, passkey entry, and out of band (OOB) methods. After the pairing process, then communications can occur between the paired devices using GATT (generic attribute profile) or another protocol.

In some cases, the pairing procedure can also include the exchange of public keys to facilitate transmission of encrypted communications using a PKI (public/private key infrastructure) type encryption scheme or PKI type communication authentication scheme. As an example of encryption, a communication can be encrypted using the public key of the intended recipient device which can only be decrypted using the private key held by the intended recipient device. As an example of communication authentication, a communication generated by a first device can be digitally signed using a private key of the first device and then the digital signature can be verified by a second device using the public key of the first device. It will be appreciated, however, that public keys can also be obtained in other ways than a direct exchange. In some embodiments, a public key can be obtained from a public key server or other network resource. In some cases, public keys, private keys, digital certificates, and the like can be exchanged after a pairing procedure has already taken place (e.g., such exchanges need not be limited to a pairing procedure).

In various scenarios, encryption/security can be itself be a part of the communication protocol standard such as security levels 1, 2, 3, and 4 and security modes 1, 2, and mixed which can be part of the BLUETOOTH® protocol standard.

Figure 2:
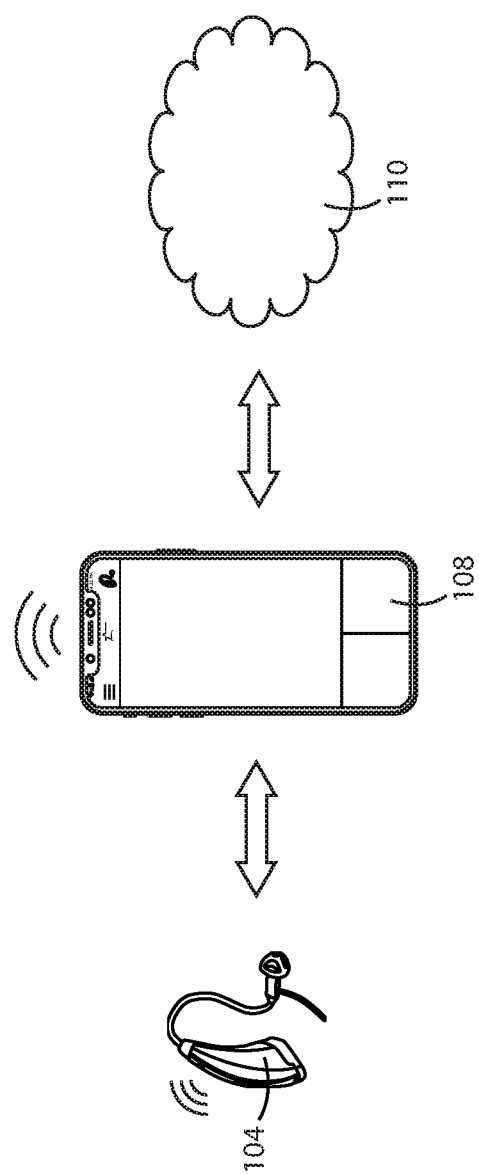
FIG. 2 is a schematic view of components of a hearing device system in accordance with embodiments herein.

Referring now to FIG. 2, a schematic view is shown of components of a hearing device system in accordance with embodiments herein. In this view, a default communication path is shown including a hearing device 104, a wireless communication enabled device 108, and the cloud 110. As referenced above, the hearing device 104 can be paired to the wireless communication enabled device 108. The wireless communication enabled device 108 can then convey communications/signals on to the cloud 110.

Many different types of communications/signals can be sent between the hearing device 104 and the wireless communication enabled device 108 including, but not limited to, data, data packets, requests, signals, notifications, alerts, warnings, advertisements, authentications, handshakes, and the like. Similarly, many different types of communications/signals can be sent between the wireless communication enabled device 108 and the cloud 110 including, but not limited to, data, data packets, requests, signals, notifications, alerts, warnings, advertisements, authentications, handshakes, and the like.

Communications/signals exchanged between the hearing device 104 and the wireless communication enabled device 108 can follow many different communication protocol standards and can be conducted through radiofrequency transmissions, inductively, magnetically, optically, or even through a wired connection in some embodiments. In particular embodiments herein, communication between the hearing device 104 and the wireless communication enabled device 108 can be conducted using a standard such as IEEE 802.11 (e.g., WIFI) or BLUETOOTH® (e.g., BLE, BLUETOOTH® 4.2 or 5.0), or ZIGBEE®, or another standard or proprietary protocol, for example.

Communications/signals exchanged between the wireless communication enabled device 108 and the cloud 110 can follow many different communication protocol standards and can be conducted through radiofrequency transmissions, inductively, magnetically, optically, or even through a wired connection in some embodiments. In particular embodiments herein, IEEE 802.11 (e.g., WIFI®) a cellular transmission protocol/platform can be used such as CDMA, cdmaOne, CDMA2000, TDMA, GSM, IS-95, LTE, 5G, GPRS, EV-DO, EDGE, UMTS, HSDPA, HSDPA, HSPA+, TD-SCDMA, WiMAX, and the like.

Figure 3:
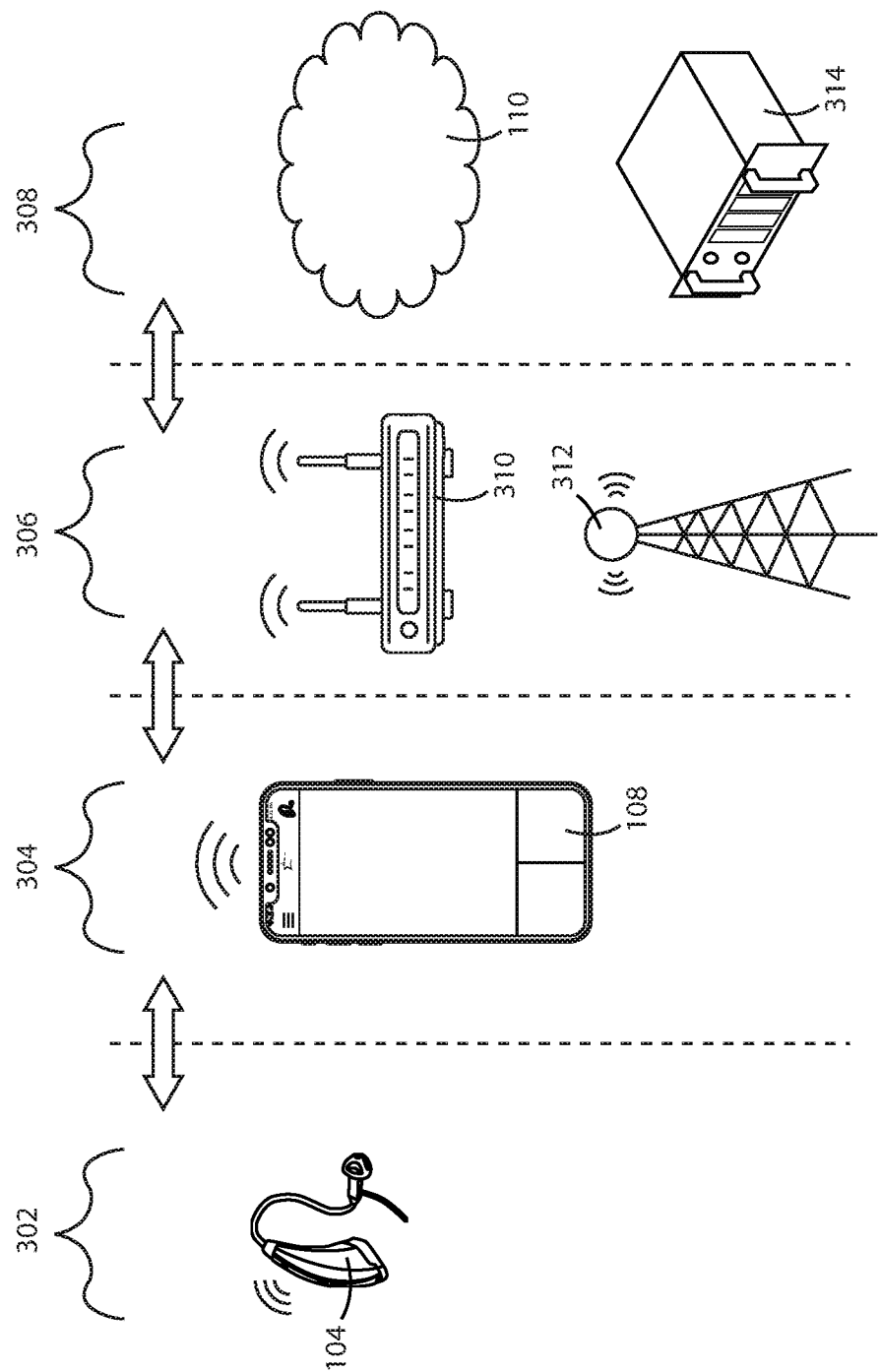
FIG. 3 is a schematic view of components of a hearing device system in accordance with embodiments herein.

It will be appreciated that various components may be involved with a default communication path from and to a hearing device. Such components can be described in terms of the layer in which they reside in a communication stack. Referring now to FIG. 3, a schematic view is shown of components of a hearing device system in accordance with embodiments herein.

The hearing device 104 can be in a device terminus layer 302. In various embodiments, data about the subject or device wearer can be generated with sensors located within the device terminus layer 302. In various embodiments, more than one device may be in the device terminus layer 302. By way of example, in some embodiment, two hearing devices 104, 106 can be in the device terminus layer 302. In some embodiments, other devices including sensors for gathering data regarding the subject or device wearer can also be within the device terminus layer 302. However, it will be appreciated that in some embodiments sensors can also be within other layers of the system.

The wireless communication enabled device 108 can be in a communication conveyance layer 304. The communication conveyance layer 304 can include one or more devices in communication with the device terminus layer 302. In some embodiments, the wireless communication enabled device 108 can be a smart phone. In some embodiments, multiple devices can be within the communication conveyance layer 304.

The wireless communication conveyance layer 304 can be in communication with a communication gateway layer 306. The communication gateway layer 306 can exchange communications with both the wireless communication conveyance layer 304 and the remote network layer 308. The communication gateway layer 306 can include various devices therein. In some embodiments, the communication gateway layer 306 can include a network router and/or modem 310 that can be configured to receive and send signals in wired or wireless modes. In some embodiments, the communication gateway layer 306 can include a cellular network tower 312 that can be configured to receive and send signals in wired or wireless modes. In various embodiments, the cellular network tower 312 can receive and send communications to the wireless communication conveyance layer 304 through wireless modes and receive and second communications to the remote network layer 308 through wired communication modes. The remote network layer 308 can include sites and/or remote computing resources in the cloud 110 and, in specific, resources such as servers 314 (real or virtual), databases, network switches, and the like.

The communication patterns/paths described with respect to FIGS. 2-3 can represent a default communication path or mode. However, it will be appreciated that sometimes communication between a hearing device 104 and a wireless communication enabled device 108 might not be possible. Stated alternately, there may be a communication breakdown between the device terminus layer 302 and the communication conveyance layer 304. There may be many reasons for such a breakdown. By way of example, causes can include distance (e.g., exceeding a threshold value), shadowing, multipath fading and the like can all cause a communication breakdown between the device terminus layer 302 and the communication conveyance layer 304.

Figure 4:
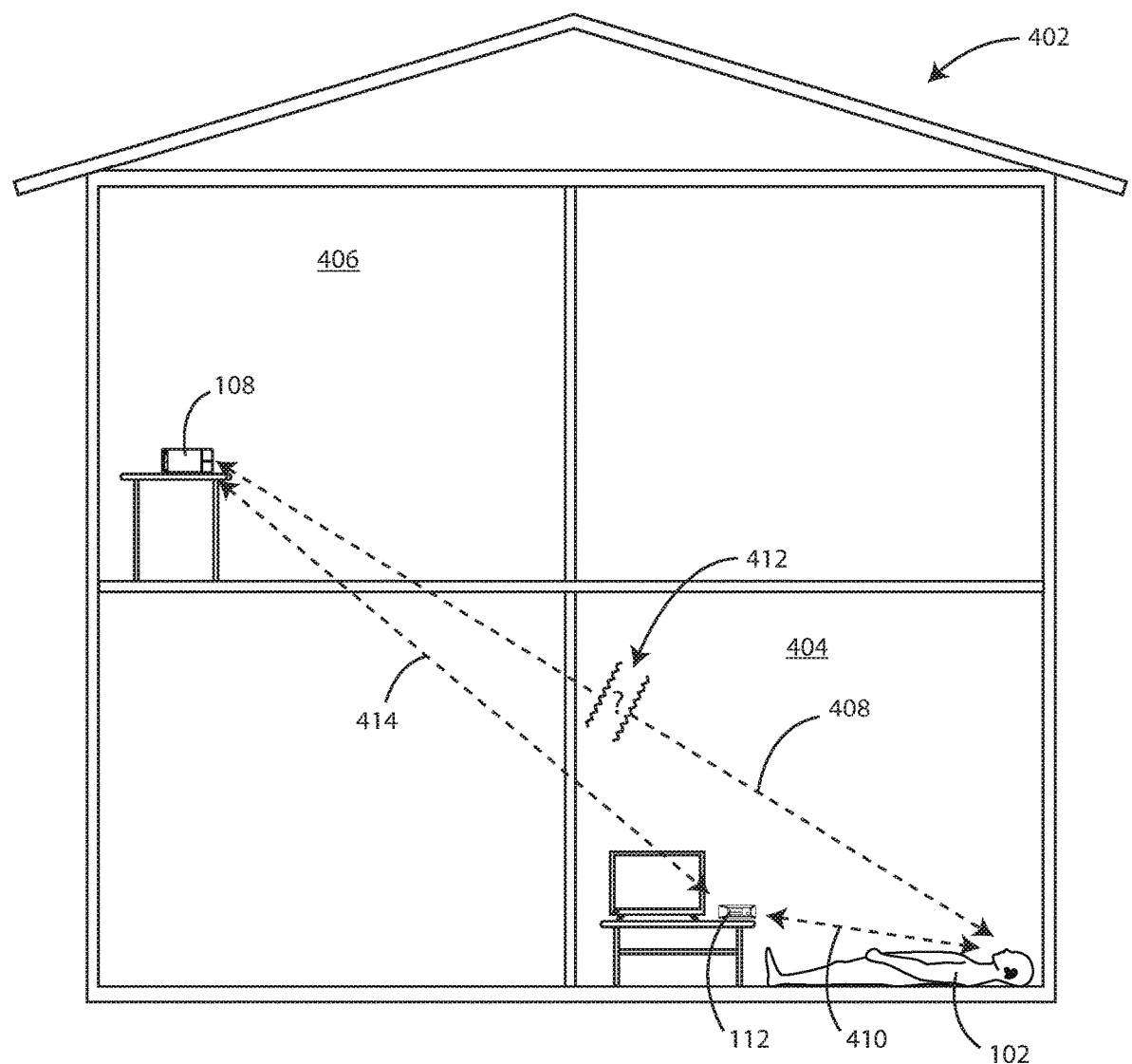
FIG. 4 is a schematic view of a communication environment in accordance with embodiments herein.

Referring now to FIG. 4, a schematic view is shown of a communication environment 402 in accordance with various embodiments herein. In this view, the communication environment 402 can be a structure or dwelling. However, it will be appreciated that the communication environment 402 can represent also represent various other physical structure/environments. In this example, a device wearer 102 can be within a first zone 404. While not shown in this view, a hearing device or devices can be worn by the device wearer 102 and are, thus, also within the first zone 404. The wireless communication enabled device 108 might be in a second zone 406 (such as set down on a night stand, counter, table or the like). However, a communication path 408 between the hearing device and the wireless communication enabled device 108 based on various factors including, distance, shadowing, multipath fading, or the like. By way of example, an obstacle 412 (which could be a metal structure) in the communication path 408 can interfere with communications between the hearing device and the wireless communication enabled device 108. Thus, there can be a communication breakdown between the device terminus layer 302 and the communication conveyance layer 304. In the case of a fall or other emergency event, this may prevent a notification originating with the hearing device from reaching the wireless communication enabled device 108 and therefore prevent help from being summoned.

Notably, however, another device such as an accessory device or hearing device accessory 112 may be in a position to be in communication with the hearing device. For example, the communication path 410 between the hearing device accessory 112 and the wireless communication enabled device 108 can be different, shorter, less-obstructed, etc. In some embodiments, communication path 410 may be similar to communication path 408, but the hearing device accessory 112 may have a higher power transmitter, better antenna, etc. Further, the hearing device accessory 112 can be capable of communication with the wireless communication enabled device 108 via communication path 414.

In some cases, the hearing device accessory 112 can be capable of communication with the wireless communication enabled device 108 as if it was paired thereto. In some cases, the hearing device accessory 112 can be temporarily paired to the wireless communication enabled device 108 as if it was paired thereto. In some cases, credentials from the hearing device can be transferred to the hearing device accessory 112 to enable communication with the wireless communication enabled device 108. In some cases, the credentials passed from the hearing device to the hearing device accessory can include one or more of a MAC address or other hardware ID, a Short Term Key (STK), a Long Term Key (LTK), a Connection Signature Resolving Key (CSRK), an Identity Resolving Key (IRK), or the like. Such credentials (e.g., a hardware address and/or encryption key of the hearing device) can be stored in non-volatile memory of the hearing device accessory.

In some embodiments, credentials from the hearing device can be transferred to the hearing device accessory 112 proactively to enable communication with the wireless communication enabled device 108. By way of example, if the system detects that a fall is likely based on factors such as postural sway, head movements, eye movements, gait analysis, etc. then the hearing device can proactively transfer credentials to the hearing device accessory 112. However, in other embodiments, a transfer of credentials does not occur unless or until the time a fall or other emergency condition occurs.

In some cases, credentials from the hearing device can be transferred to the hearing device accessory 112 using security that is comparable to security used to transmit information between paired devices, such as the hearing device being paired to the wireless communication enabled device 108. For example, in some cases, the hearing device and the hearing device accessory 112 can be securely paired together using procedures as described herein.

Thus, in accordance with various embodiments herein, the hearing device accessory 112 can be used as a proxy for the hearing device in order to get communications out from the device terminus layer 302 and on to the communication conveyance layer 304. This can represent a non-default communication path or mode or an emergency or secondary communication path or mode.

In functioning as a proxy device for the hearing device in various embodiments herein, the accessory does not merely represent just an additional hop in a communication chain. Rather, the accessory comes to possess the credentials (e.g., MAC address or other hardware ID, Long Term Key (LTK), Connection Signature Resolving Key (CSRK), Identity Resolving Key (IRK), or the like) of the hearing device and thus, for communication purposes, effectively becomes the hearing device itself.

Thus, in various embodiments herein, the system can operate in a first communication mode and a second communication mode. The first communication mode can include the hearing device being paired to a wireless communication enabled device for conveying data to a non-local network as initiated by the hearing device. The system operates in the first communication mode when the hearing device can communicate with the wireless communication enabled device. The first communication mode can be preferential in the sense that whenever communication is possible between the hearing device and the wireless communication enabled device, the system will operate in the first communication mode.

The second communication mode can include the hearing device accessory operating as being paired to the wireless communication enabled device for conveying data to the non-local network as initiated by the hearing device.

The system can enter the second communication mode under various circumstances. By way of example, the system can enter the second communication mode when the hearing device cannot communicate with the wireless communication enabled device. In some embodiments, the system can enter the second communication mode only when both the hearing device detects a fall or other emergency scenario or the device wearer requests help and when the hearing device cannot communicate with the wireless communication enabled device.

In various embodiments, the hearing device periodically sends advertising data packets to test communication between the hearing device and the wireless communication enabled device. For example, the hearing device can send advertising data packets to test communication between the hearing device and the wireless communication enabled device every 100 milliseconds, 500 milliseconds, 1 second, 5 second, 30 seconds, 60 seconds, 5 minutes, or 10 minutes. In various embodiments, the hearing device accessory periodically scans for advertising data packets sent from the hearing device.

In some embodiments, the system can be alerted to a possible fall or other emergency situation by a notification from the hearing device, which could be a communication specifying the fall or emergency state or could be advertising data packets sent from the hearing device with a fall event flag. In some embodiments, the system can enter the second communication mode by the hearing device sending advertising data packets with a fall event flag or other transmissions (packet based or otherwise) with fall information and this being received by another device of the system, such as the hearing device accessory.

Beyond the hearing device accessory becoming a proxy for the hearing device, various other steps can take place when the system enters the second communication mode to optimize the system for successful communication of an emergency communication. For example, in some embodiments the system disconnects from all non-essential devices upon entering the second communication mode. In some embodiments, all non-essential advertising data is removed from packets coming from the hearing device upon entering the second communication mode to keep the packets as small as possible.

Even before actually entering the second communication mode, in some embodiments various steps can take place when a possible fall or other emergency situation is detected by the system and/or the system receives a notification of a fall or other emergency situation from the hearing device or another device or as input from the device wearer. For example, in some embodiments a radio transmitter (or transceiver) power of the hearing device and the hearing device accessory is increased to a maximum supported level after a possible fall event is detected by the system. In some embodiments intervals between advertising packet transmissions are reduced after a possible fall event is detected by the system. In some embodiments, the hearing device sends advertising packets encoded with forward error correction after a possible fall event is detected by the system. In some embodiments, the hearing device can send packets in a long-range mode including the use of lower data rates with forward error correction or encoding to obtain a significant link margin advantage.

Figure 5:
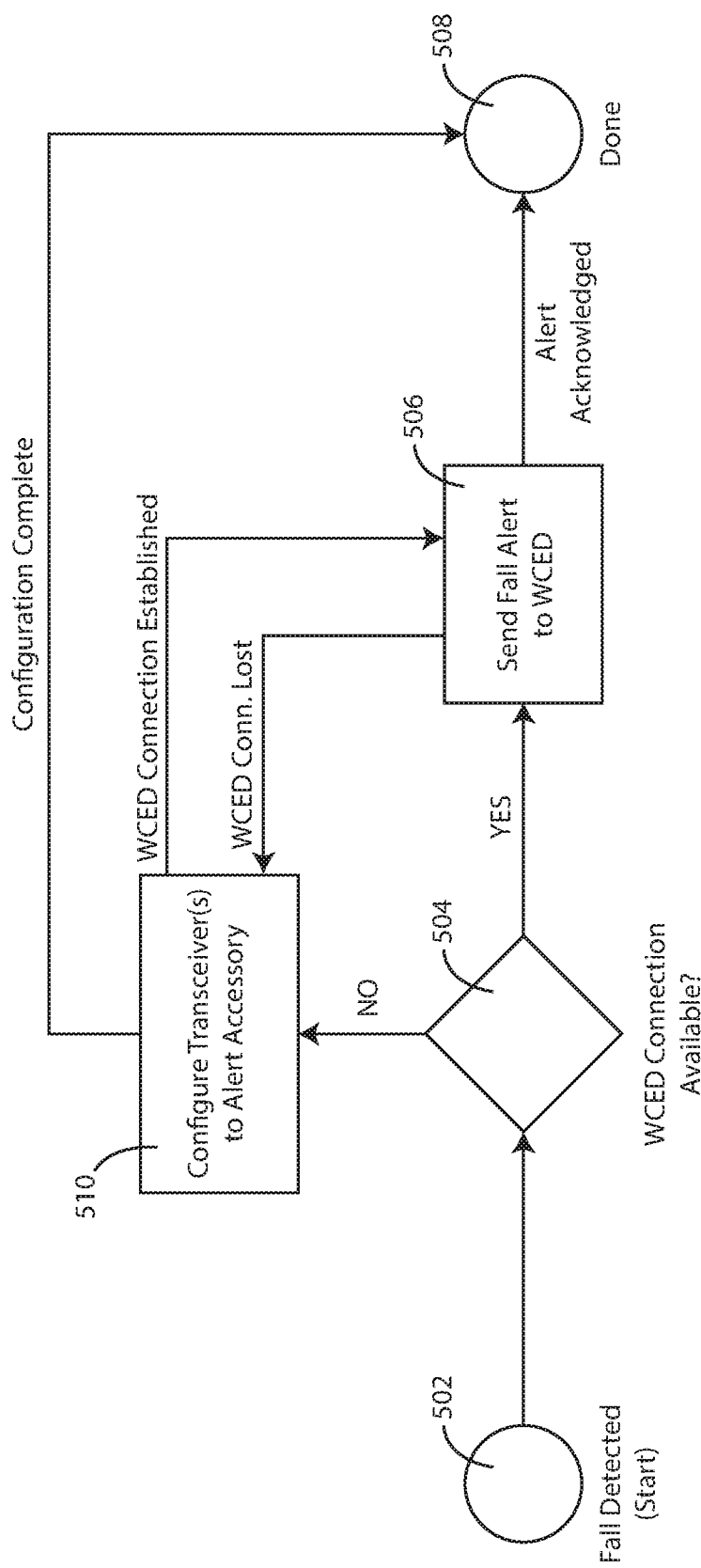
FIG. 5 is a schematic diagram of operations of a hearing device in response to a detected fall or other emergency event scenario.

Referring now to FIG. 5, a schematic diagram is shown of operations of a hearing device in response to a detected fall or other emergency event scenario. The sequence of operations depicted in FIG. 5 can begin with detection of a fall 502 or other emergency event (such as a detected state that is potentially hazardous to the device wearer's health or wellbeing). Next, the hearing device can check the status of communication with a wireless communication enabled device (WCED) 504. If the WCED connection is available, the hearing device can send 506 a fall alert message to the WCED. In this case, an acknowledgement of the fall alert message completes 508 the scenario.

However, if a WCED connection is not available, the hearing device can attempt to coordinate with its binaural peer (e.g., the other hearing device within a pair) to verify that the other hearing device also does not have a WCED connection and that both devices are aware of the fall event. If neither hearing device has a WCED connection, then both hearing devices can configure 510 their transceivers to alert an accessory device. In specific, one or both hearing devices can change the advertising packets sent out such that they contain a fall event flag. The fall event flag can use a registered universal unique identifier (UUID) so that other non-hearing device devices don't cause a false alert. By way of example an advertising packet may include elements such as a preamble, access address, CRC, BLUETOOTH address of the sender, and an advertising payload, amongst other things. In various embodiments, the advertising payload can be up to 31 bytes long and, specifically, can include flags, such as a fall event (or other emergency event) flag.

One or both of the hearing devices can also disconnect from all non-essential devices to preserve radio baseband resources. One or both of the devices can also remove non-essential advertising data to keep the packets as small as possible. This can maximize the probability of reception in interference and in an AWGN (additive white gaussian noise) channel. One or both devices can also increase the transceiver transmit power to the maximum supported level. However, in some embodiments, if a low battery condition is detected this step can be skipped. One or both devices can also decrease the advertisement interval to the minimum permitted value so that packets are transmitted at higher frequency. However, in some embodiments, if a low battery condition is detected then this step can be skipped.

In some embodiments herein, the system can provide an opportunity for the device wearer or another individual to clear or cancel a false alarm or a fall which does not require assistance. For example, detection of a fall 502 may also include audible, haptic or visual notification to the device wearer and receiving user input from them to cancel the process if the detection was not accurate or did not result in a scenario requiring assistance. In some embodiments, the system can pause for a defined period of time after detection of a possible fall such as 1, 5, 10, 30, or 60 seconds before proceeding to allow time for the device wearer to cancel the process.

Embodiments herein can include scenarios involving one or two hearing devices. However, there can some advantages to the use of two hearing devices. For example, since both hearing devices can be sending advertising packets with a fall event flag set, antenna spatial diversity is achieved further increasing communication range between the hearing devices and an accessory device that can serve as a proxy device.

Figure 6:
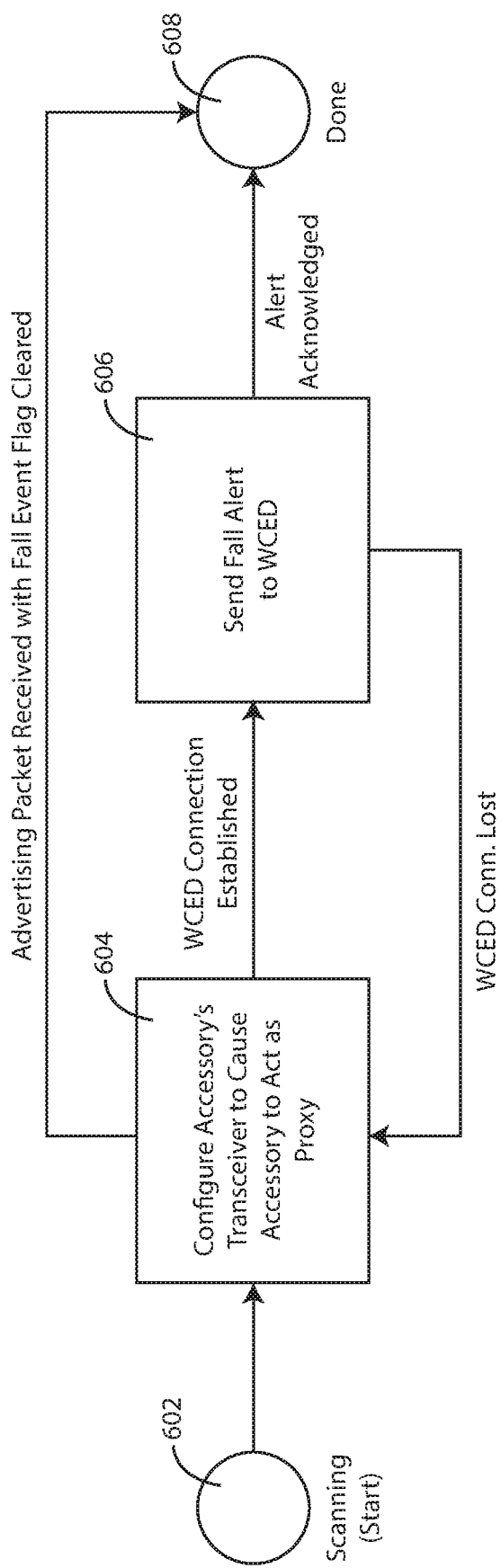
FIG. 6 is a schematic diagram of operations of a hearing device accessory in response to a detected fall or other emergency event scenario.

Referring now to FIG. 6, a schematic diagram is shown of operations of a hearing device accessory in response to a detected fall or other emergency event scenario. In this scenario, a hearing device accessory is scanning 602 for advertising packets from previously paired hearing devices. The hearing device accessory then receives an advertisement packet from a paired hearing device with the fall event flag set. The hearing device accessory then configures 604 its transceiver to connect to the WCED. Configuration can include various specific steps. For example, hearing device accessory configures its transceiver to transmit at the maximum permitted power level. The hearing device accessory can also configure its transceiver to have improved sensitivity by activating an LNA mode on an external RF front end. Increasing sensitivity via an external LNA also makes the communication chain more susceptible to blocking and wideband interference. If increasing sensitivity is not initially successful due to such cases, the LNA can be bypassed or have its gain reduced in continued efforts to establish communication. The hearing device accessory can configure the transceiver to be a GAP peripheral with the same MAC address as the hearing device from which the advertising packet was received. The hearing device accessory can configure the transceiver to only accept connections from the targeted WCED. The hearing device accessory can configure the transceiver to use the hearing devices' encryption keys and authentication information so that the connection does not get rejected by the WCED.

If the hearing device accessory establishes a connection to the WCED, a fall alert message is sent 606. If the message is acknowledged, then the sequence can be complete 608. However, if the WCED connection is suddenly lost prior to acknowledgement, the hearing device accessory can continue to try to establish the connection. Also, if an advertising packet is received with the fall event flag cleared from the device that originally sent it, then sequence is complete 608.

Figure 7:
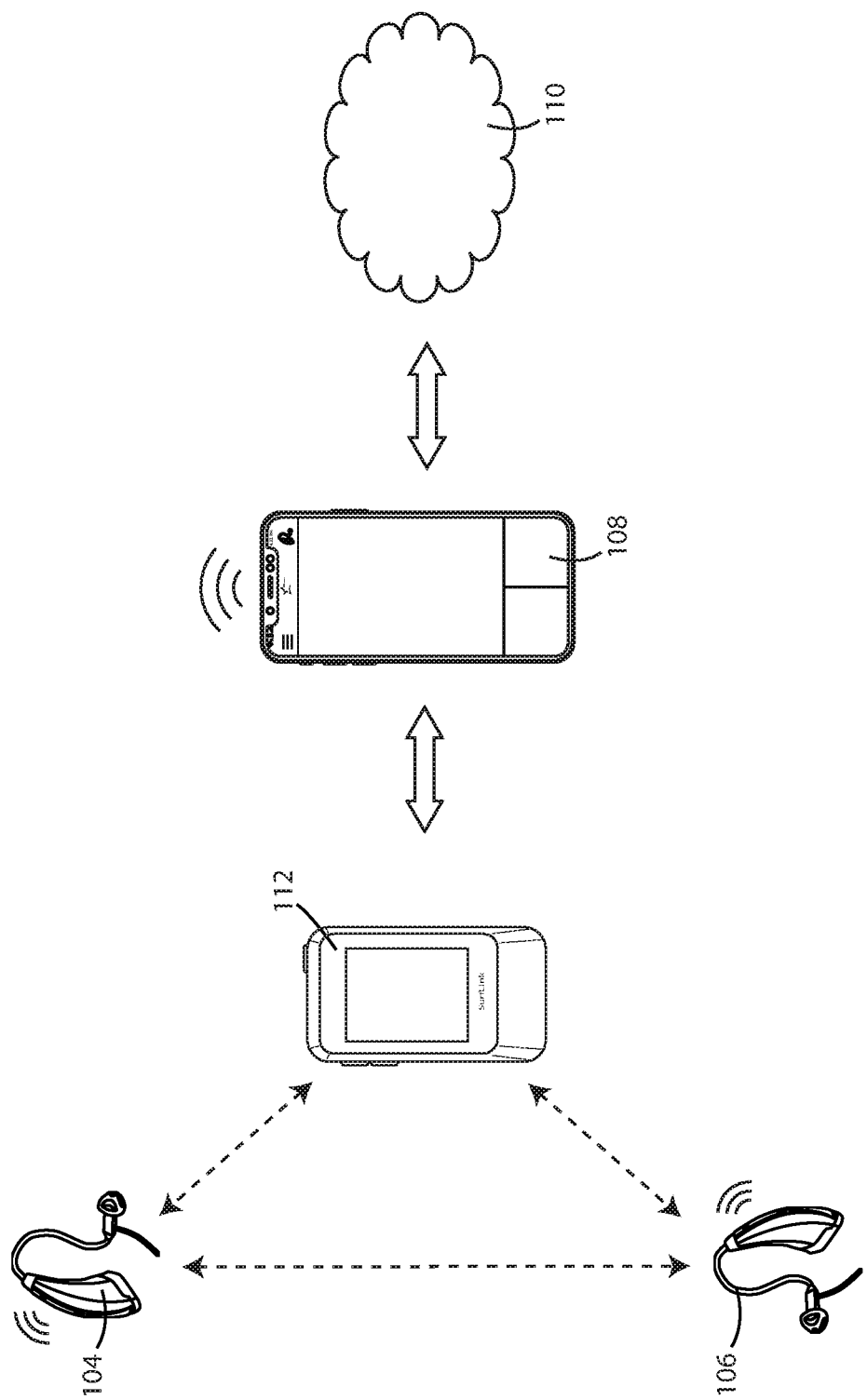
FIG. 7 is a schematic view of components of a hearing device system in accordance with embodiments herein.

Referring now to FIG. 7, a schematic view is shown of components of a hearing device system in accordance with various embodiments herein. In this view, a non-default communication path or mode or an emergency or secondary communication path or mode is illustrated. The hearing device 104 can send communications to and receive communications from the hearing device accessory 112. In some cases, a second hearing device 106 can send communications to and receive communications from the hearing device accessory 112. In some cases, the hearing device 104 can send communications to and receive communications from the second hearing device 106 and vice versa.

The hearing device accessory 112 can send communications to and receive communications from the wireless communication enabled device 108. The wireless communication enabled device 108 can send communications to and receive communications from the cloud 110. In various embodiments, the wireless communication enabled device 108 can attempt to provide a confirmation back to the hearing device wearer that it has conveyed data along to the cloud 110 or other non-local network. Such a confirmation communication can follow the same path through the network, but in reverse. However, in some embodiments, such a confirmation communication may follow a different communication path. In some embodiments, the system can route a confirmation communication as a command can be sent to a home automation system to provide a visual notification to the user (such as the lights flashing on and off) or another type of notification. In some embodiments, after the hearing device accessory 112 has conveyed data on to wireless communication enabled device 108 and/or received verification that the wireless communication enabled device 108 has conveyed data on to the cloud 110 or other non-local network, the hearing device accessory 112 can disconnect from the wireless communication enabled device 108. This can allow the hearing device(s) to reconnect to the wireless communication enabled device 108 in the event of a false alarm for cancellation.

Figure 8:
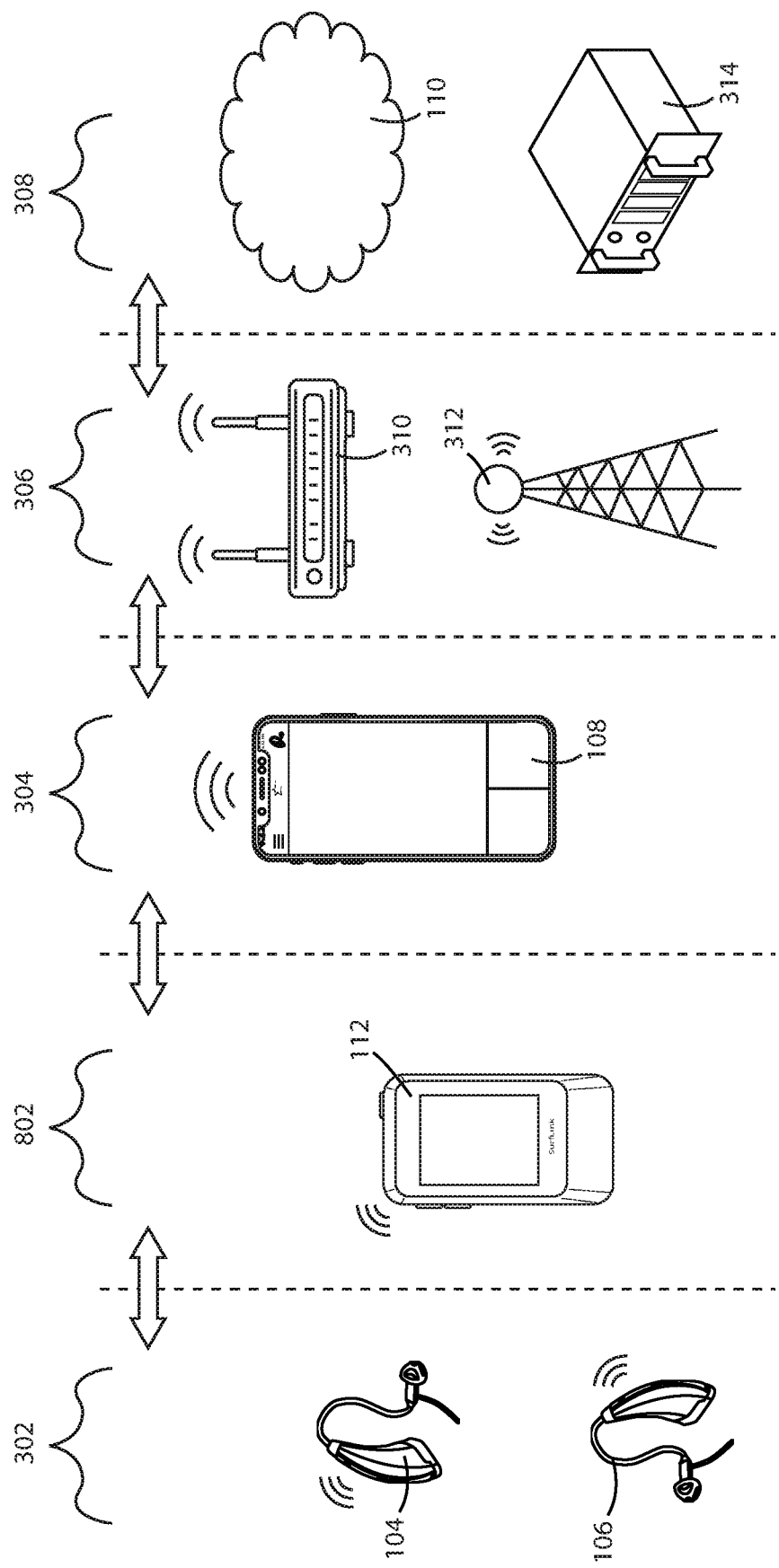
FIG. 8 is a schematic view of components of a hearing device system in accordance with embodiments herein.

Referring now to FIG. 8, a schematic view is shown of components of a hearing device system in accordance with various embodiments herein. In this view, a non-default communication path or mode or an emergency or secondary communication path or mode is illustrated with respect to layers of a system. The hearing devices 104, 106 can be in a device terminus layer 302 as previously described. The hearing device accessory 112 can be in a hearing device proxy layer 802. The device terminus layer 302 can send data to and receive data from the hearing device proxy layer 802. The hearing device proxy layer 802 can also send data to and receive data from the communication conveyance layer 304. The communication conveyance layer 304, as described before, can be in communication with a communication gateway layer 306. As described before, the communication gateway layer 306 can be in communication with a remote network layer 308.

Figure 9:
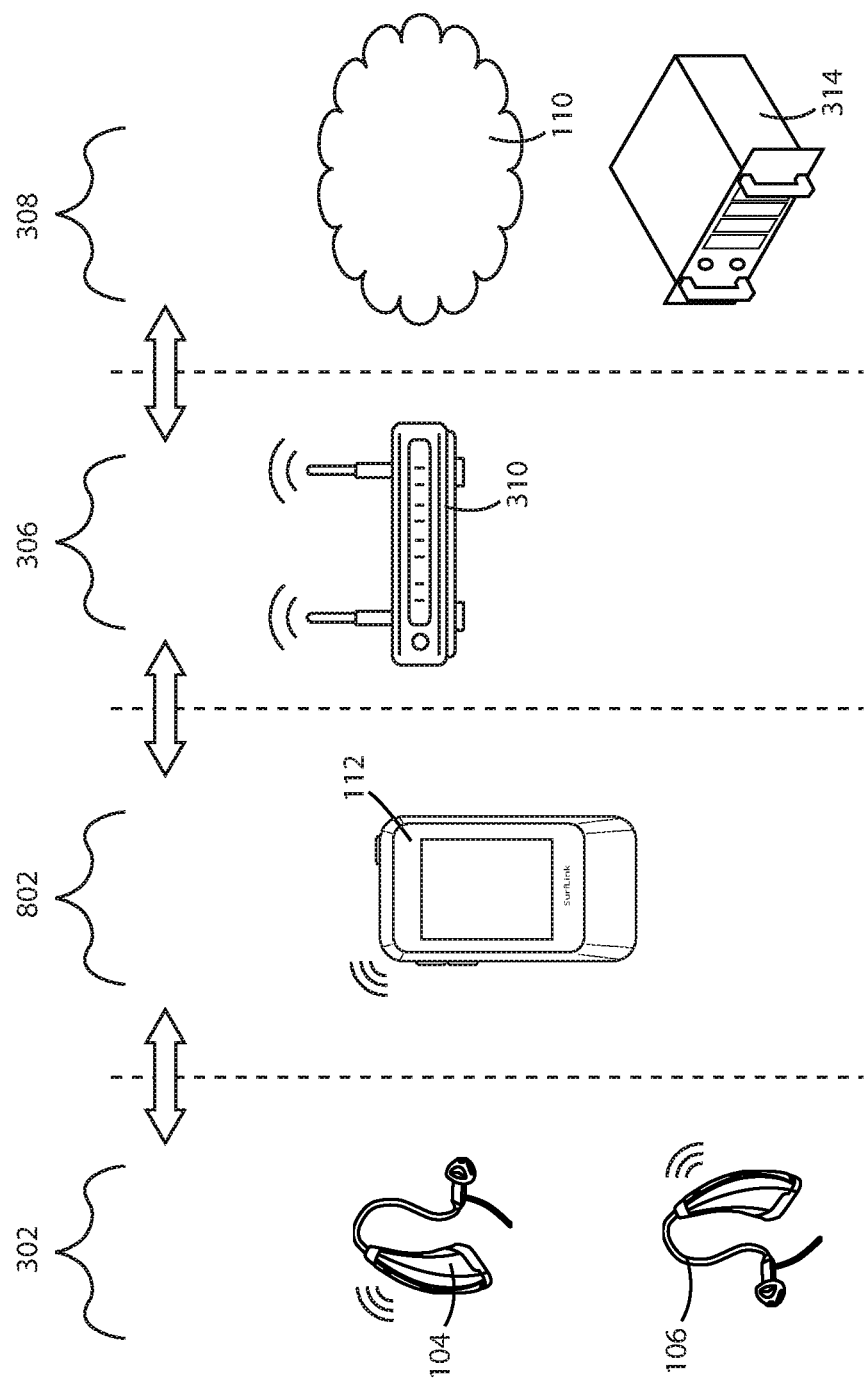
FIG. 9 is a schematic view of components of a hearing device system in accordance with embodiments herein.

In some cases, communication can bypass the communication conveyance layer 304. Referring now to FIG. 9, a schematic view is shown of components of a hearing device system in accordance with various embodiments herein. In this view, another embodiment of a non-default communication path or mode or an emergency or secondary communication path or mode is illustrated with respect to layers of a system. The hearing devices 104, 106 can be in a device terminus layer 302 as previously described. The hearing device accessory 112 can be in a hearing device proxy layer 802. The device terminus layer 302 can send data to and receive data from the hearing device proxy layer 802. The hearing device proxy layer 802 can bypass the communication conveyance layer 304 and be in communication with a communication gateway layer 306 that, in turn, can be in communication with a remote network layer 308.

In some embodiments, communications may pass between multiple devices within the hearing device proxy layer. However, in various embodiments, only the hearing device accessory that directly communicates with the communication conveyance layer 304 acts as a true proxy for the hearing device(s) in that it receives information from the hearing device(s) so that it can communicate with a wireless communication enabled device 108 as if directly paired thereto.

Figure 10:
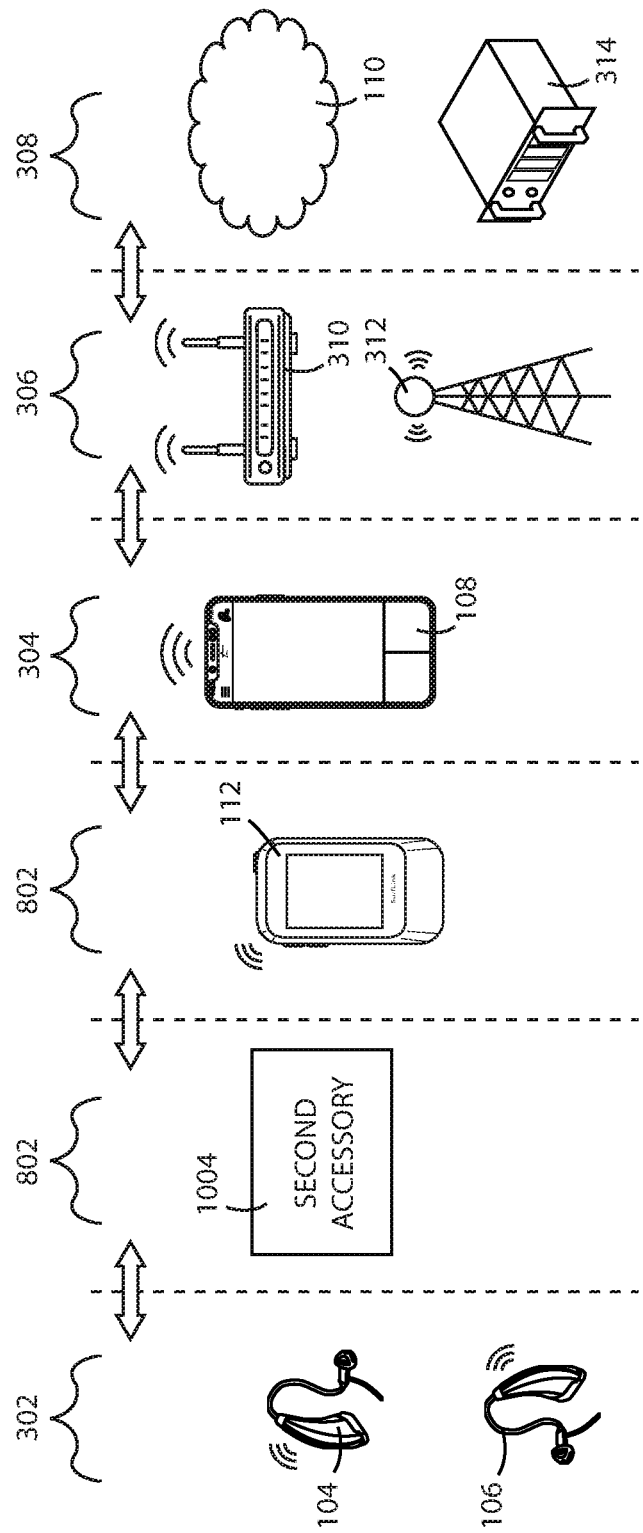
FIG. 10 is a schematic view of components of a hearing device system in accordance with embodiments herein.

Referring now to FIG. 10, a schematic view is shown of components of a hearing device system in accordance with various embodiments herein. In this view, another embodiment of a non-default communication path or mode or an emergency or secondary communication path or mode is illustrated with respect to layers of a system. The hearing devices 104, 106 can be in a device terminus layer 302 as previously described. The hearing device accessory 112 and a second hearing device accessory 1004 can be in a hearing device proxy layer 802. The device terminus layer 302 can send data to and receive data from the hearing device proxy layer 802. The second hearing device accessory 1004 can exchange communications with the hearing device accessory 112. The hearing device proxy layer 802 can also send data to and receive data from the communication conveyance layer 304. The communication conveyance layer 304, as described before, can be in communication with a communication gateway layer 306. As described before, the communication gateway layer 306 can be in communication with a remote network layer 308.

In various embodiments where more than one hearing device accessory may be present, advertising communications with a fall event flag can be forwarded from accessory to accessory. For example, when a first accessory receives advertising communications with a fall event flag, it can undertake procedures such as described with respect to FIG. 6. However, if it cannot successfully establish a connection with a wireless communication enabled device, then it can attempt to forward the advertising communications with a fall event flag on to another accessory device that may be able to establish a connection with the wireless communication enabled device. If the second accessory receives the advertising communications with a fall event flag, it can then try to establish a connection with the wireless communication enabled device.

Hearing devices, including hearing aids and hearables (e.g., wearable earphones), can include an enclosure, such as a housing or shell, within which internal components are disposed. Components of a hearing device herein can include a control circuit, digital signal processor (DSP), memory (such as non-volatile memory), power management circuitry, a data communications bus, one or more communication devices (e.g., a radio, a near-field magnetic induction device), one or more antennas, one or more microphones, a receiver/speaker, and various sensors as described in greater detail below. More advanced hearing devices can incorporate a long-range communication device, such as a BLUETOOTH® transceiver or other type of radio frequency (RF) transceiver.

Figure 11:
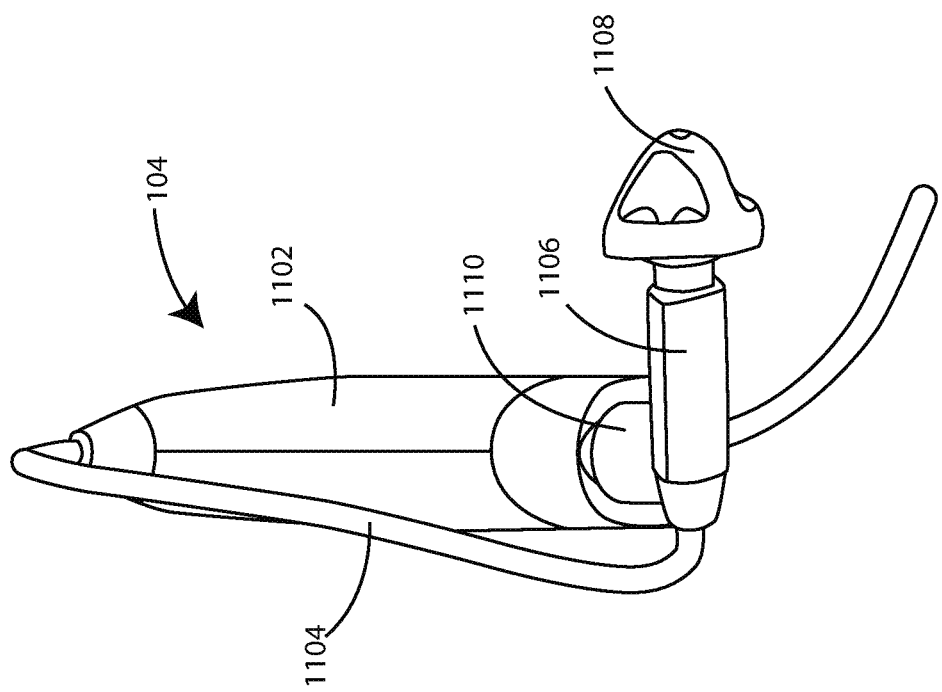
FIG. 11 is a schematic view of a hearing device in accordance with various embodiments herein.

Referring now to FIG. 11, a schematic view of a hearing device 104 is shown in accordance with various embodiments herein. The hearing device 104 can include a hearing device housing 1102. The hearing device housing 1102 can define a battery compartment 1110 into which a battery can be disposed to provide power to the device. The battery can be of various types, such as a primary battery (using various chemistries including, but not limited to, zinc-air or the like) or a secondary battery (e.g., rechargeable using various chemistries including, but not limited to, lithium ion). The hearing device 104 can also include a receiver 1106 adjacent to an earbud 1108. The receiver 1106 an include a component that converts electrical impulses into sound, such as an electroacoustic transducer, speaker, or loud speaker. A cable 1104 or connecting wire can include one or more electrical conductors and provide electrical communication between components inside of the hearing device housing 1102 and components inside of the receiver 1106.

The hearing device 104 shown in FIG. 11 is a receiver-in-canal type device and thus the receiver is designed to be placed within the ear canal. However, it will be appreciated that may different form factors for hearing devices are contemplated herein. As such, hearing devices herein can include, but are not limited to, behind-the-ear (BTE), in-the-ear (ITE), in-the-canal (ITC), invisible-in-canal (IIC), receiver-in-canal (RIC), receiver in-the-ear (RITE) and completely-in-the-canal (CIC) type hearing devices.

Hearing devices of the present disclosure can incorporate an antenna arrangement coupled to a high-frequency radio, such as a 2.4 GHz radio. The radio can conform to an IEEE 802.11 (e.g., WIFI®), BLUETOOTH® (e.g., BLE, BLUETOOTH® 4.2 or 5.0) or ZIGBEE® specification, for example, or another standard or proprietary wireless specification. It is understood that hearing devices of the present disclosure can employ other radios, such as a 900 MHz radio or radios operating at other frequencies or frequency bands. Hearing devices of the present disclosure can be configured to receive streaming audio (e.g., digital audio data or files) from an electronic or digital source. Representative electronic/digital sources (also referred to herein as accessory devices) include an assistive listening system, a TV streamer, a radio, a smartphone, a cell phone/entertainment device (CPED) or other electronic device that serves as a source of digital audio data or files. Systems herein can also include these types of accessory devices as well as other types of devices.

Figure 12:
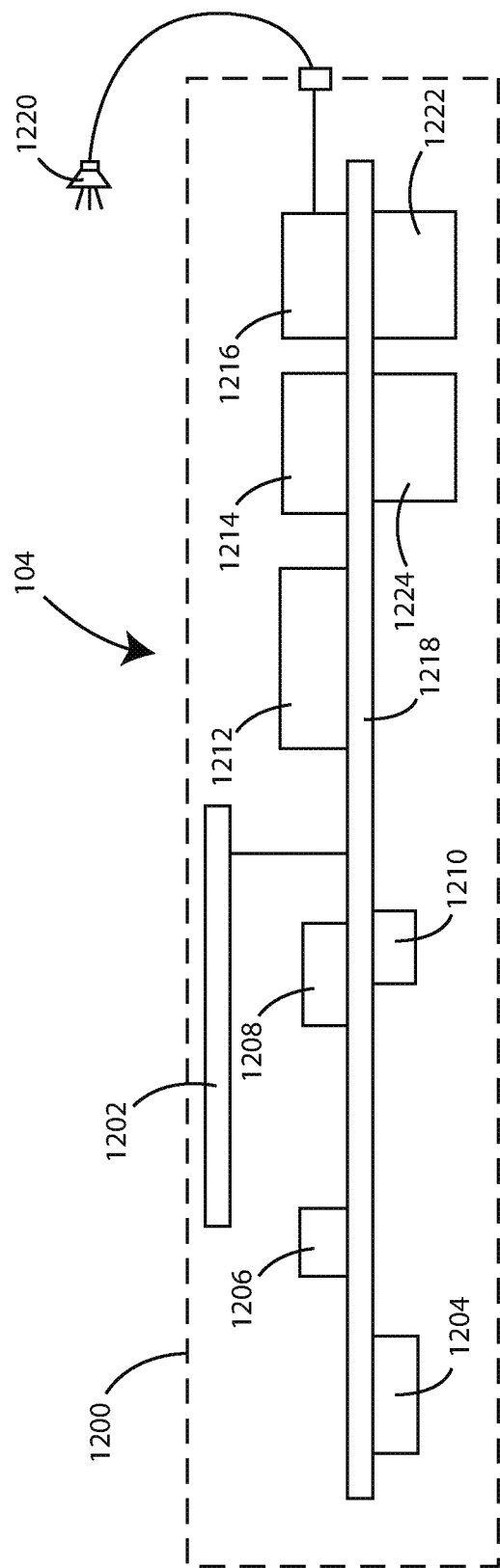
FIG. 12 is a schematic block diagram of various components of a hearing device in accordance with various embodiments herein.

Referring now to FIG. 12, a schematic block diagram is shown with various components of a hearing device in accordance with various embodiments. The block diagram of FIG. 12 represents a generic hearing device for purposes of illustration. The hearing device 104 shown in FIG. 12 includes several components electrically connected to a flexible mother circuit 1218 (e.g., flexible mother board) which is disposed within housing 1200. A power supply circuit 1204 can include a battery and can be electrically connected to the flexible mother circuit 1218 and provides power to the various components of the hearing device 104. One or more microphones 1206 are electrically connected to the flexible mother circuit 1218, which provides electrical communication between the microphones 1206 and a digital signal processor (DSP) 1212. Among other components, the DSP 1212 incorporates or is coupled to audio signal processing circuitry configured to implement various functions described herein. A sensor package 1214 can be coupled to the DSP 1212 via the flexible mother circuit 1218. The sensor package 1214 can include one or more specific types of sensors such as those described in greater detail below. One or more user switches 1210 (e.g., on/off, volume, mic directional settings) are electrically coupled to the DSP 1212 via the flexible mother circuit 1218.

An audio output device 1216 is electrically connected to the DSP 1212 via the flexible mother circuit 1218. In some embodiments, the audio output device 1216 comprises a speaker (coupled to an amplifier). In other embodiments, the audio output device 1216 comprises an amplifier coupled to an external receiver 1220 adapted for positioning within an ear of a wearer. The external receiver 1220 can include an electroacoustic transducer, speaker, or loud speaker. The hearing device 104 may incorporate a communication device 1208 coupled to the flexible mother circuit 1218 and to an antenna 1202 directly or indirectly via the flexible mother circuit 1218. The communication device 1208 can be a Bluetooth® transceiver, such as a BLE (Bluetooth® low energy) transceiver or other transceiver(s) (e.g., an IEEE 802.11 compliant device, a ZIGBEE® device, or another standard or proprietary wireless standard transceiver). The communication device 1208 can be configured to communicate with one or more external devices, such as those discussed previously, in accordance with various embodiments. In various embodiments, the communication device 1208 can be configured to communicate with an external visual display device such as a smart phone, a video display screen, a tablet, a computer, or the like.

In various embodiments, the hearing device 104 can also include a control circuit 1222 and a memory storage device 1224. The control circuit 1222 can be in electrical communication with other components of the device. The control circuit 1222 can execute various operations, such as those described herein. The control circuit 1222 can include various components including, but not limited to, a microprocessor, a microcontroller, an FPGA (field-programmable gate array) processing device, an ASIC (application specific integrated circuit), or the like. The memory storage device 1224 can include both volatile and non-volatile memory. The memory storage device 1224 can include ROM, RAM, flash memory, EEPROM, SSD devices, NAND chips, and the like. The memory storage device 1224 can be used to store data from sensors as described herein and/or processed data generated using data from sensors as described herein.

Hearing device accessories herein can include, but are not limited to, a charger, a cell phone transmitter, a media streamer, a hearing aid remote, a USB dongle device, and a remote microphone.

Figure 13:
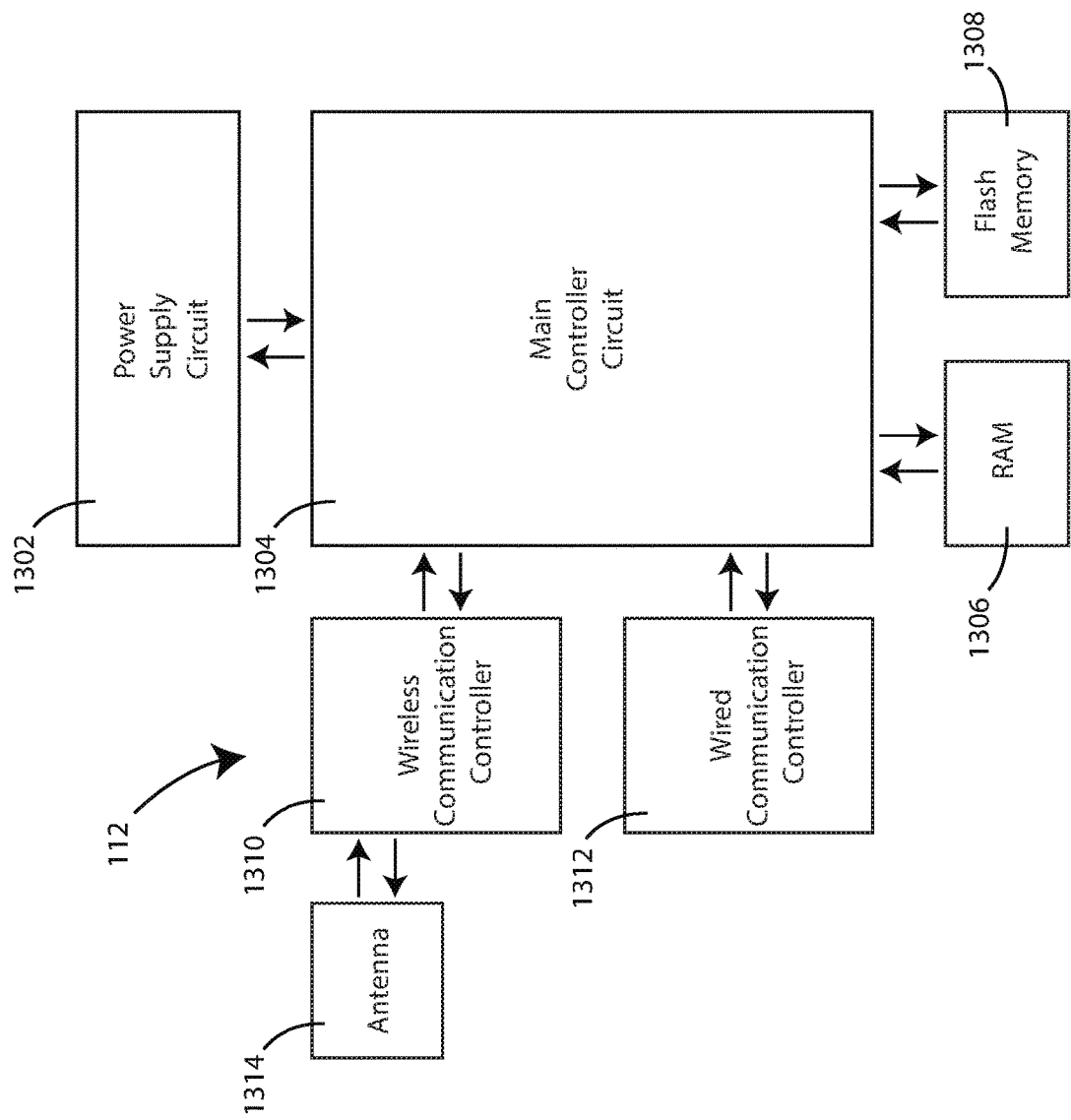
FIG. 13 is a schematic block diagram of various components of a hearing device accessory in accordance with various embodiments herein.

Referring now to FIG. 13, a schematic block diagram is shown of various components of an exemplary hearing device accessory 112 in accordance with various embodiments herein. The hearing device accessory 112 can include a main controller circuit 1304. The main controller circuit 1304 can include components such as a microprocessor, a microcontroller, an FPGA (field-programmable gate array) processing device, an ASIC (application specific integrated circuit), or the like. The main controller circuit 1304 can also include components for internal wired communication (e.g., communication amongst components of the hearing device accessory 112) such as I$^2$C (inter-integrated circuit bus) components and SPI (serial peripheral interface bus) components.

The hearing device accessory 112 can also include a power supply circuit 1302. In some cases, the hearing device accessory 112 can be adapted to be powered by an AC current source, and thus the power supply circuit 1302 can include a rectifier to convey DC current on to the main controller circuit and/or other components such as a transformer, voltage regulator, and the like. However, in some cases, the hearing device accessory 112 can be adapted to be powered by a DC current source and/or a battery such as a primary or secondary battery and so the power supply circuit 1302 may include a transformer and/or other components such as a voltage regulator and the like. The hearing device accessory 112 can also include memory, such as RAM 1306, and non-volatile memory such as flash memory 1308. Memory of the hearing device accessory 112 can include, but is not limited to, ROM, RAM, flash memory, EEPROM, SSD devices, NAND chips, and the like.

In various embodiments, the hearing device accessory 112 can also include a wireless communication controller 1310 that can control, facilitate, and/or enable wireless communication and can be in communication with an antenna 1314. The wireless communication controller 1310 can be configured to send and receive communications at various frequencies and using various wireless protocols including, but not limited to, WIFI®, BLUETOOTH®, ZIGBEE®, and the like. The wireless communication controller 1310 can include hardware components such as a wireless receiver, wireless transmitter, wireless transceiver, and the like. In some embodiments, the communication controller 1310 and the antenna 1314 can be integrated.

In some embodiments, the maximum power of wireless transmissions of the wireless communication controller 1310 can be greater than the maximum power of wireless transmissions of the hearing device. In some embodiments, the maximum power of wireless transmissions of the wireless communication controller 1310 can be about −20, −15, −10, −5, −1, 0, 1, 2, 3, 4, 5, 6, 7, 8, 10, 12, 15, 20, 25, 30, 40, or 50 dBm, or an amount falling within a range between any of the foregoing. In some embodiments, the maximum power of wireless transmissions of the wireless communication controller 1310 can be at least about 50, 100, 200, 300, 400, 500, 600, 700, 800, 900, or 1000 percent greater than the maximum power of wireless transmissions of the hearing device. In some embodiments, the maximum power of wireless transmissions of the wireless communication controller 1310 can be at least about 0.005, 0.01, 0.1, 0.5, 1, 2, 3, 4, 5, 8, 10, 20, 30, 40, 50, 60, 70, 80, 90, or 100 watts higher than the maximum power of wireless transmissions of the hearing device, or can be an amount falling within a range between any of the foregoing.

In various embodiments, the hearing device accessory 112 can also be in communication with a wired communication controller 1312. The wired communication controller 1312 be connected to jacks of various types to receive a wire or cable and can provide for communication over the wire or cable using serial or parallel approaches. In some embodiments, the wired communication controller can be configured to communicate using wired standards including, but not limited to, Ethernet, RS-232, RS-485, USB, and the like, and hardware components such as a UART, a USART, and the like. It will be appreciated that hearing device accessories herein can also include various other components including, but not limited to, a speaker, a microphone, sensors, a battery, clock circuit, and the like.

Fall Detection

Hearing devices herein can include fall detection that benefit from natural human biomechanics which often act to steady and protect the head. By way of example, the velocity of the head during a fall collision can be a key metric for gauging the severity of the fall impact. Due to placement of a hearing device on or in the ear, such devices are less susceptible to spurious movements than fall detection devices that a worn on other parts of the body, e.g. on an arm or hung around the neck. With fewer artifacts to manage, in addition to having the greatest distance to fall, head-worn fall detection devices such hearing devices herein can be tuned to capture a greater number of falls, including those with softer impacts or slower transitions, as are frequently observed among older adults. In addition, hearing devices can be ideal for detection of falls since individuals with hearing loss are also at a higher risk for falls.

Various embodiments of devices, systems and methods herein can provide a high rate of sensitivity while mitigating the rate of false positives. In various embodiments herein, motions sensor data and/or other sensor data from a one or a binaural set (pair) of hearing devices can be used to more accurately detect falls and therefore maintain high sensitivity while reducing false-positives. In various embodiments herein, the wearer of a device such as a hearing device (as part of a binaural set of devices or as a single device) can be provided with an opportunity to actively cancel a fall alert that is a false-positive. In various embodiments, machine learning techniques can be applied to data gathered from devices such as hearing devices and possible accessories along with paired data regarding whether the gathered data related to true-positive or false-positive fall occurrences in order to further enhance fall detection sensitivity and reduce false-positives.

By tracking motion using one or more motion sensors (and in some cases other types of sensors also) and evaluating data from the same, patterns or signatures indicative of a fall can be detected. In some embodiments, patterns or signatures indicative of a fall can include a detected rapid downward movement of a subject's head and/or other body parts (e.g., sudden height change), downward velocity exceeding a threshold value followed by a sudden stop. In some embodiments, patterns or signatures of a fall can include a detected rapid rotation of a subject's head, such as from an upright position to a non-upright position. In various embodiments, patterns or signatures indicative of a fall can include multiple factors including, for example, a rapid downward movement, downward velocity exceeding a threshold value followed by a sudden stop, or a downward rotation of a subject's head and/or other body parts along with other aspects including one or more of the subject's head remaining at a non-upright angle for at least a threshold amount of time, the subject's body in a prone, supine or lying on side position for at least a threshold amount of time, sound indicating an impact, sound indicating a scream, and the like. In some embodiments, the signal strength of wireless communications between various devices may be used to determine the position of an individual, relative to various reflective or absorptive surfaces, at various phases of a fall event, such as the ground.

In some embodiments, devices (hearing devices or accessories) and/or systems herein are configured to evaluate data from one or more sensors to detect a possible fall of a subject in physical contact with the hearing device by evaluating at least one of timing of steps and fall detection phases (including, but not limited to a pre-fall phase, a falling phase, an impact phase, and a resting phase), degree of acceleration changes, peak acceleration changes, activity classification, and posture changes.

In some embodiments herein, patterns or signatures of a fall for a particular subject can be enhanced over time through machine learning analysis. For example, the subject (or a third party) can provide input as to the occurrence of falls and/or the occurrence of false-positive events. These occurrences of falls and/or false positives can be paired with data representing data gathered at the time of these occurrences. Then, an approach such as a supervised machine learning algorithm can be applied in order to derive a pattern or signature consistent with a fall and/or a false positive. In this way, the pattern or signature can be updated over time to be more accurate both for a specific subject as well as for a population of subjections.

In some embodiments, an assessed fall risk can be used as a factor in determining whether a fall has occurred. For example, a fall risk can be calculated according to various techniques, including, but not limited to techniques described in U.S. Publ. Pat. Appl. Nos. 2018/0228405; 2018/0233018; and 2018/0228404, the content of which is herein incorporated by reference. The assessed fall risk can then be applied such that the system is more likely to indicate that a fall has occurred if the assessed fall risk was relatively high immediately before the occurrence in question. In some embodiments, the assessed fall risk can be applied transitorily such that the system is only more likely to indicate that a fall has occurred for a period of seconds or minutes. In other embodiments, the assessed fall risk can be applied over a longer period of time.

In some embodiments, device settings can include a fall detection sensitivity setting such that the subject or a third party can change the device or system settings such that the fall detection criteria becomes more or less sensitive.

In some embodiments, the device wearer can issue a command to indicate that they have fallen. For example, the device wearer can speak a particular word or words to indicate that they have fallen or otherwise need assistance. In some embodiments, the device wearer can press a button on the hearing device to indicate that they have fallen or otherwise need assistance.

In some embodiments, a log of detected falls can be stored by one or more devices of the system and periodically provided to the user or a third party, such as a responsible third party and/or a care provider. In some embodiments, a log of near-falls or balance events can be stored by one or more devices of the system and periodically provided to the user or a third party, such as a responsible third party and/or a care provider. A near-fall herein can be an occurrence that fails to qualify as a fall, but comes close thereto (such as missing the criteria for a fall be less than 5%, 10%, 20%, or 30% for example).

Aspects of evaluating data to detect possible falls are described in greater detail in U.S. Publ. Pat. Appl. Nos. 2018/0228404 and 2018/0233018, the content of which is herein incorporated by reference.

Sensors

Hearing devices herein can include one or more sensor packages (including one or more discrete or integrated sensors) to provide data. The sensor package can comprise one or a multiplicity of sensors. In some embodiments, the sensor packages can include one or more motion sensors amongst other types of sensors. Motion sensors herein can include inertial measurement units (IMU), accelerometers, gyroscopes, barometers, altimeters, and the like. The IMU can be of a type disclosed in commonly owned U.S. patent application Ser. No. 15/331,230, filed Oct. 21, 2016, which is incorporated herein by reference. Motions sensors can be used to track movement of a patient in accordance with various embodiments herein.

In some embodiments, the motion sensors can be disposed in a fixed position with respect to the head of a patient, such as worn on or near the head or ears. In some embodiments, the motion sensors can be worn on or near another part of the body such as on a wrist, arm, or leg of the patient.

According to various embodiments, the sensor package can include one or more of an IMU, and accelerometer (3, 6, or 9 axis), a gyroscope, a barometer, an altimeter, a magnetometer, a magnetic sensor, an eye movement sensor, a pressure sensor, an acoustic sensor, a telecoil, a heart rate sensor, a global positioning system (GPS), a temperature sensor, a blood pressure sensor, an oxygen saturation sensor, an optical sensor, a blood glucose sensor (optical or otherwise), a galvanic skin response sensor, a cortisol level sensor (optical or otherwise), a microphone, acoustic sensor, an electrocardiogram (ECG) sensor, electroencephalography (EEG) sensor which can be a neurological sensor, eye movement sensor (e.g., electrooculogram (EOG) sensor), myographic potential electrode sensor (EMG), a heart rate monitor, a pulse oximeter, a wireless radio antenna, blood perfusion sensor, hydrometer, sweat sensor, cerumen sensor, air quality sensor, pupillometry sensor, cortisol level sensor, hematocrit sensor, light sensor, image sensor, and the like.

In some embodiments, the sensor package can be part of a hearing device. However, in some embodiments, the sensor packages can include one or more additional sensors that are external to a hearing device. For example, various of the sensors described above can be part of a wrist-worn or ankle-worn sensor package, or a sensor package supported by a chest strap.

Data produced by the sensor(s) of the sensor package can be operated on by a processor of the device or system.

As used herein the term "inertial measurement unit" or "IMU" shall refer to an electronic device that can generate signals related to a body's specific force and/or angular rate. IMUs herein can include one or more accelerometers (3, 6, or 9 axis) to detect linear acceleration and a gyroscope to detect rotational rate. In some embodiments, an IMU can also include a magnetometer to detect a magnetic field.

The eye movement sensor may be, for example, an electrooculographic (EOG) sensor, such as an EOG sensor disclosed in commonly owned U.S. Pat. No. 9,167,356, which is incorporated herein by reference. The pressure sensor can be, for example, a MEMS-based pressure sensor, a piezo-resistive pressure sensor, a flexion sensor, a strain sensor, a diaphragm-type sensor and the like.

The temperature sensor can be, for example, a thermistor (thermally sensitive resistor), a resistance temperature detector, a thermocouple, a semiconductor-based sensor, an infrared sensor, or the like.

The blood pressure sensor can be, for example, a pressure sensor. The heart rate sensor can be, for example, an electrical signal sensor, an acoustic sensor, a pressure sensor, an infrared sensor, an optical sensor, or the like.

The oxygen saturation sensor (such as a blood oximetry sensor) can be, for example, an optical sensor, an infrared sensor, or the like.

The electrical signal sensor can include two or more electrodes and can include circuitry to sense and record electrical signals including sensed electrical potentials and the magnitude thereof (according to Ohm's law where V=IR) as well as measure impedance from an applied electrical potential.

It will be appreciated that the sensor package can include one or more sensors that are external to the hearing device. In addition to the external sensors discussed hereinabove, the sensor package can comprise a network of body sensors (such as those listed above) that sense movement of a multiplicity of body parts (e.g., arms, legs, torso). In some embodiments, the hearing device can be in electronic communication with the sensors or processor of another medical device, e.g., an insulin pump device or a heart pacemaker device.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A hearing device system comprising:
a wearable hearing device comprising
a control circuit;
a motion sensor in electrical communication with the control circuit;
a microphone in electrical communication with the control circuit;
an electroacoustic transducer for generating sound in electrical communication with the control circuit; a transceiver in electrical communication with the control circuit;
a power supply circuit in electrical communication with the control circuit;
a non-wearable hearing device accessory;
wherein the system operates in a first communication mode and a second communication mode;
the first communication mode comprising the wearable hearing device being paired to a wireless communication enabled device for conveying emergency data to a non-local network as initiated by the wearable hearing device;
wherein the system operates in the first communication mode when the wearable hearing device has a communication connection with the wireless communication enabled device;
the second communication mode comprising the non-wearable hearing device accessory being paired to the wireless communication enabled device for conveying the emergency data initiated by the wearable hearing device to the non-local network via the non-wearable hearing device accessory;
wherein the system operates in the second communication mode when the wearable hearing device does not have a communication connection with the wireless communication enabled device;
wherein the non-wearable hearing device accessory uses a hardware address of the wearable hearing device to communicate with the wireless communication enabled device as if the non-wearable hearing device accessory was paired to the wireless communication enabled device.

2. The hearing device system of claim 1, the non-wearable hearing device accessory comprising at least one of:
   a charger;
   a cell phone transmitter;
   a media streamer;
   a hearing aid remote;
   a USB dongle device; and
   a remote microphone.

3. The hearing device system of claim 1, further comprising a second wearable hearing device.

4. The hearing device system of claim 1, wherein the system operates in the second communication mode when the wearable hearing device and the second wearable hearing device cannot communicate with the wireless communication enabled device.

5. The hearing device system of claim 1, wherein the conveyed emergency data relates to a notification of a possible fall event.

6. The hearing device system of claim 5, wherein the possible fall event is identified based on data from the motion sensor.

7. The hearing device system of claim 1, wherein the wireless communication enabled device attempts to provide a confirmation back to a wearable hearing device wearer that it has conveyed the emergency data to the non-local network.

8. The hearing device system of claim 1, wherein the system operates in the second communication mode when the wearable hearing device is unable to establish a link to the wireless communication enabled device due to at least one of:
   the wearable hearing device is disposed at a distance from the wireless communication enabled device that exceeds a maximum communication distance between the wearable hearing device and the wireless communication enabled device;
   shadowing;
   interference; and
   multipath fading.

9. The hearing device system of claim 1, wherein the wearable hearing device periodically sends advertising data packets to test communication between the wearable hearing device and the wireless communication enabled device.

10. The hearing device system of claim 1, wherein the non-wearable hearing device accessory periodically scans for advertising data packets sent from the wearable hearing device.

11. The hearing device system of claim 1, wherein the hardware address of the wearable hearing device and an encryption key of the wearable hearing device are stored in a non-volatile memory of the non-wearable hearing device accessory.

12. The hearing device system of claim 1, wherein the system operates in the second communication mode by including a fall event flag with advertising data sent by the wearable hearing device.

13. The hearing device system of claim 1, wherein the system disconnects from all non-essential devices upon entering the second communication mode.

14. The hearing device system of claim 1, wherein all non-essential advertising data from the wearable hearing device is removed upon entering the second communication mode.

15. The hearing device system of claim 1, wherein a radio transmitter power of the wearable hearing device and the non-wearable hearing device accessory is increased to a maximum supported level after a possible fall event is detected by the system.

16. The hearing device system of claim 1, wherein intervals between advertising packet transmissions are reduced after a possible fall event is detected by the system.

17. The hearing device system of claim 1, wherein the wearable hearing device sends advertising packets encoded with forward error correction after a possible fall event is detected by the system.

18. The hearing device system of claim 1, the wearable hearing device and the non-wearable hearing device accessory each comprising a power transmitter, wherein the power transmitter of the non-wearable hearing device accessory has higher power than the power transmitter of the wearable hearing device.

19. A method of conveying emergency notifications from a wearable hearing device comprising:
   detecting a possible fall or other emergency event with the wearable hearing device;
   sending advertising packets or other communications from the wearable hearing device including an emergency flag of the possible fall or the other emergency event when an emergency event is detected;
   detecting whether communication exists between the wearable hearing device and a wireless communication enabled device;
   sending an emergency data transmission from the wearable hearing device to the wireless communication enabled device and onto a non-local data communication network when communication exists between the wearable hearing device and the wireless communication enabled device;
   when communication does not exist between the wearable hearing device and the wireless communication enabled device, detecting whether communication exists between the wearable hearing device and a non-wearable hearing device accessory; and
   sending the emergency data transmission from the wearable hearing device to the non-wearable hearing device accessory and onto the wireless communication enabled device and the non-local data communication network when communication exists between the wearable hearing device and the non-wearable hearing device accessory.

20. A method of conveying emergency notifications from a wearable hearing device comprising:
   detecting a possible fall or other emergency event with the wearable hearing device;
   sending advertising packets or other communications from the wearable hearing device including an emergency flag of the possible fall or the other emergency event when an emergency event is detected;
   detecting whether communication exists between the wearable hearing device and a wireless communication enabled device;
   sending an emergency data transmission from the wearable hearing device to the wireless communication enabled device and onto a non-local data communication network when communication exists between the wearable hearing device and the wireless communication enabled device;
   when communication does not exist between the wearable hearing device and the wireless communication enabled device, detecting whether communication exists between the wearable hearing device and a non-wearable first hearing device accessory; and sending the emergency data transmission from the wearable hearing device to the non-wearable first hearing device accessory, from the non-wearable first hearing device accessory to a non-wearable second hearing device accessory and onto the wireless communication enabled device and the non-local data communication network when communication exists between the wearable hearing device and the non-wearable first hearing device accessory.

* * * * *